(12) United States Patent
Theuer et al.

(10) Patent No.: US 8,017,618 B2
(45) Date of Patent: Sep. 13, 2011

(54) ANTIFOLATE AGENT COMBINATIONS IN THE TREATMENT OF CANCER

(75) Inventors: Charles P. Theuer, Carlsbad, CA (US); Bonne Jean Adams, San Diego, CA (US)

(73) Assignee: Tracon Pharmaceuticals, Inc., San Diego, CA (US)

( * ) Notice: Subject to any disclaimer, the term of this patent is extended or adjusted under 35 U.S.C. 154(b) by 46 days.

(21) Appl. No.: 11/963,644

(22) Filed: Dec. 21, 2007

(65) Prior Publication Data

US 2008/0234298 A1 Sep. 25, 2008

Related U.S. Application Data

(60) Provisional application No. 60/877,836, filed on Dec. 29, 2006, provisional application No. 60/883,266, filed on Jan. 3, 2007, provisional application No. 60/883,959, filed on Jan. 8, 2007.

(51) Int. Cl.
*A61K 31/519* (2006.01)
*A61K 31/131* (2006.01)

(52) U.S. Cl. ..................... 514/265.1; 514/645

(58) Field of Classification Search ............... 514/265.1, 514/645

See application file for complete search history.

(56) References Cited

U.S. PATENT DOCUMENTS

| | | | |
|---|---|---|---|
| 6,190,661 B1 | 2/2001 | Kelley et al. | |
| 6,406,917 B1 | 6/2002 | Kelley | |
| 6,465,448 B1 * | 10/2002 | Gerson et al. | 514/183 |
| 6,635,677 B2 * | 10/2003 | Gerson et al. | 514/645 |
| 2004/0071761 A1 | 4/2004 | Miller et al. | |
| 2006/0088515 A1 | 4/2006 | Higuchi et al. | |
| 2006/0142231 A1 | 6/2006 | Ashworth et al. | |
| 2006/0241186 A1 | 10/2006 | Gerson et al. | |
| 2007/0082841 A1 | 4/2007 | Higuchi et al. | |
| 2007/0185013 A1 | 8/2007 | Clark | |
| 2007/0208134 A1 | 9/2007 | Hunter et al. | |

FOREIGN PATENT DOCUMENTS

| | | |
|---|---|---|
| CN | 1846679 | 10/2006 |
| WO | WO-03-007955 A2 | 1/2003 |
| WO | WO-03-070234 A | 8/2003 |

OTHER PUBLICATIONS

Alm et al., "Effects of Topically Applied PGF2α and Its Isopropylester on Normal and Glaucomatous Human Eyes," Prog. Clin. Biol. Res. 312:447-458 (1989).
Barret, J.M. et al., "Novel artificial endonucleases inhibit base excision repair and potentiate the cytotoxicity of DNA-damaging agents on L1210 cells," Anti-Cancer Drugs 10:55-65 (1999).
Caldecott et al., "XRCCI polypeptide interacts with DNA polymerase β and possibly poly (ADP-ribose) polymerase, and DNA ligase III is a novel molecular 'nick-sensor' in vitro," Nucleic Acids Res. 24:4387-4394 (1996).

Helma et al., "A public domain image-analysis program for the single-cell gel-electrophoresis (comet) assay," Mutation Res. 466:9-15 (2000).
Kim, J.H. et al., "Cytotoxic effects of premetrexed in gastric cancer cells," Cancer Science 96:365-371 (2005).
Joshi, A., "Microparticulates for Ophthalmic Drug Delivery," J. Ocul. Pharmacol. 10(1):29-45 (1994).
Liu et al., "Prevention of base excision repair by TRC102 (methoxyamine) potentiates the anti-tumor activity of pemetrexed in vitro and in vivo," J. Clin. Onc. 25(185-Jun. 20 Suppl): 13005 (2007) Poster Presentation/Abstract.
Liu et al., "Blockage of abasic site repair enhances antitumor efficacy of 1,3-bis-(2-chloroethyl)-1-nitrosourea in colon tumor xenografts," Molecular Cancer Therapeutics 2:1061-1066 (2003).
Liu et al., "Base Excision Repair as a Therapeutic Target in Colon Cancer," Clin. Cancer Res. 8:2985-2991 (2002).
Liu et al., "Pharmacologic Disruption of Base Excision Repair Sensitizes Mismatch Repair-deficient and -proficient Colon Cancer Cells to Methylating Agents," Clin. Cancer Res. 5:2908-2917 (1999).
Mayer et al., "Efficacy of a Novel Hydrogel Formulation in Human Volunteers," Ophthalmologica 210(2):101-103 (1996).
Molinete et al., "Over production of the poly (ADP-ribose)polymerase DNA-binding domain blocks alkylation-induced DNA repair synthesis in mammalian cells," EMBO J. 12:2109-2117 (1993).
Mordenti, "Intraocular Pharmacokinetics and Safety of a Humanized Monoclonal Antibody in Rabbits after Intravitreal Administration of a Solution of a Solution or a PLGA Microsphere Formulation," Toxicol. Sci. 52(1):101-106 (1999).
Nakamura et al., "Highly Sensitive Apurinic/Apyrimidinic Site Assay Can Detect Spontaneous and Chemically Induced Depurination under Physiological Conditions," Cancer Res. 58:222-225 (1998).
Neddermann et al., "Functional expression of soluble human interleukin-11 (IL-11) receptor alpha and stoichiometry of in vitro IL-11 receptor complexes with gp130," J. Biol. Chem. 271:12767-12776 (1996).
O'Connor et al., "Isolation and structure of a cDNA expressing a mammlaian 3- methyladenine-DNA glycosylase," EMBO J. 9:3337-3342 (1990).
Olsen et al., "Molecular cloning of human uracil-DNA glycosylase, a highly conserved DNA repair enzyme," EMBO J. 8:3121-3125 (1989).
Radicella et al., "Cloning and characterization of hOGG1, a human homolog of the OGGI gene of Saccharomyces cerevisiae," PNAS USA 94:8010-7015 (1997).

(Continued)

*Primary Examiner* — James D Anderson
(74) *Attorney, Agent, or Firm* — Wilson Sonsini Goodrich & Rosati

(57) ABSTRACT

Compositions and methods useful in the treatment of certain cancers. The methods include administering, to a patient receiving an antifolate anticancer agent, methoxyamine administered in an amount sufficient to enhance or increase the effect of the antifolate anticancer agent. In part, this application is based on the recognition that certain molecules that target abasic lesions or AP sites in DNA improve, augment, or potentiate the chemotherapeutic efficacy of certain anticancer agents.

36 Claims, 7 Drawing Sheets

OTHER PUBLICATIONS

Rosenquist et al., "Cloning and characterization of mammalian 8-oxoguanine DNA glycosylase," PNAS USA 94:7429-8434 (1997).

Samson et al., Cloning and characterization of a 3-methyladenine DNA glycosylase cDNA from human cells whose gene maps to chromosome 16,: PNAS USA 88:9127-9131 (1991).

Shedden et al., "Efficacy and Tolerability of Timolol Maleate Ophthalmic Gel-Forming Solution Versus Timolol Ophthalmic Solution in Adults with Open-Angle Glaucoma or Ocular Hypertension: A Six-Month, Double-Masked, Multicenter Study," Clin. Ther. 23(3):440-450 (2001).

Shewach, D.S. and Lawrence, T.S., "Antimetabolite Radiosensitizers," J. Clin. Oncol. 25(26):4043-4050 (2007).

Van Triest, B. et al., "Thymidylate synthase level as the main predictor parameter for sensitivity to 5-FU but not for Folate-based Themidylate Synthase Inhibitors in 13 Nonselected Colon Cancer Cell Lines," Clin. Cancer Res. 5:643-654 (1999).

Vollberg et al., "Isolation and characterization of the human uracil DNA glycolase gene," PNAS USA 86:8693-9697 (1989).

Wilson, "Mammalain base excision repair and DNA polymerase beta," Mutation Res. 407:203-215 (1998).

Gerson et al., "458 Invited Base excision repair inhibition: a new target for cancer therapy," Eur. J. Cancer Suppl. 4(12):140-141 (2006).

Richards et al., "Misincorporation of deoxyuridine in human cells: consequences of antifolate exposure," Basic Life Sciences 31:149-162 (1985).

PCT/US07/088666 Search Report dated Nov. 18, 2009.

Fishel et al., "Manipulation of base excision repair to sensitize ovarian cancer cells to alkylating agent temozolomide," Clin. Cancer Res. 13(1):260-267 (2007).

Van Der Bogaert et al., "Pemetrexed maintenance therapy in patients with malignant pleural mesothelioma," J. Thorac. Oncol. 1(1):25-30 (2006).

Rollins et al., "Pemetrexed: a multitargeted antifolate," Clin. Ther. 27(9):1343-1382 (2005).

* cited by examiner

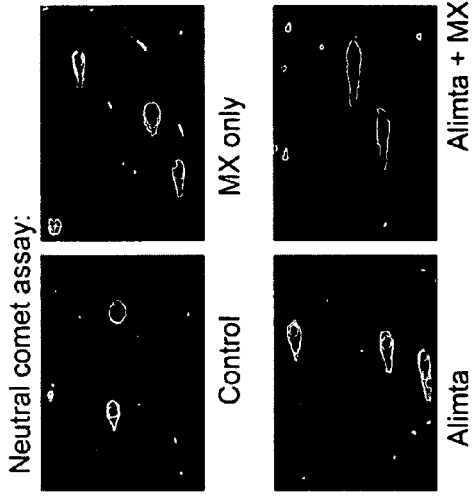
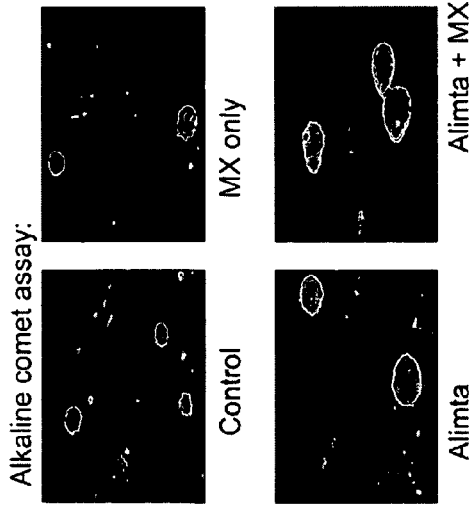
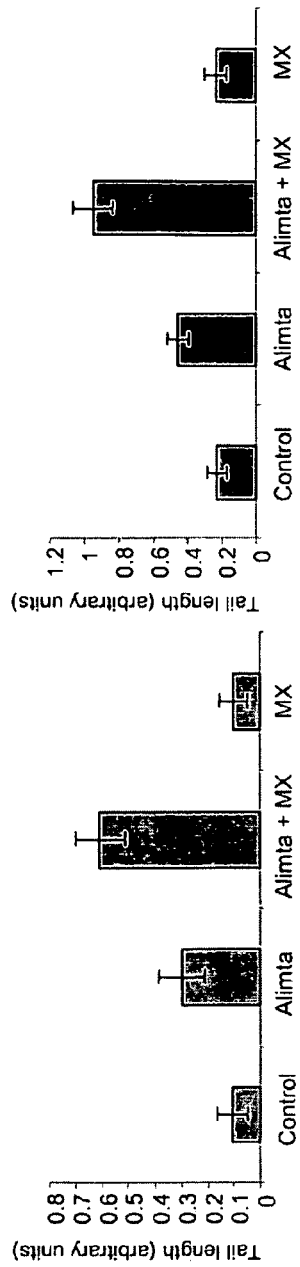
DNA Strand Breaks Measured by Comet Assay in H460 Cells 4 hr after Treatments
Fig. 1A
Fig. 1B
Fig. 1C
Fig. 1D Fig. 2  Mean TRC102 Concentration in Plasma from Male Sprague Dawley Rats at Different Time Points After a Single Bolus Dosing of TRC102 via Intravenous and Oral Administration at 20 mg/kg Body Weight

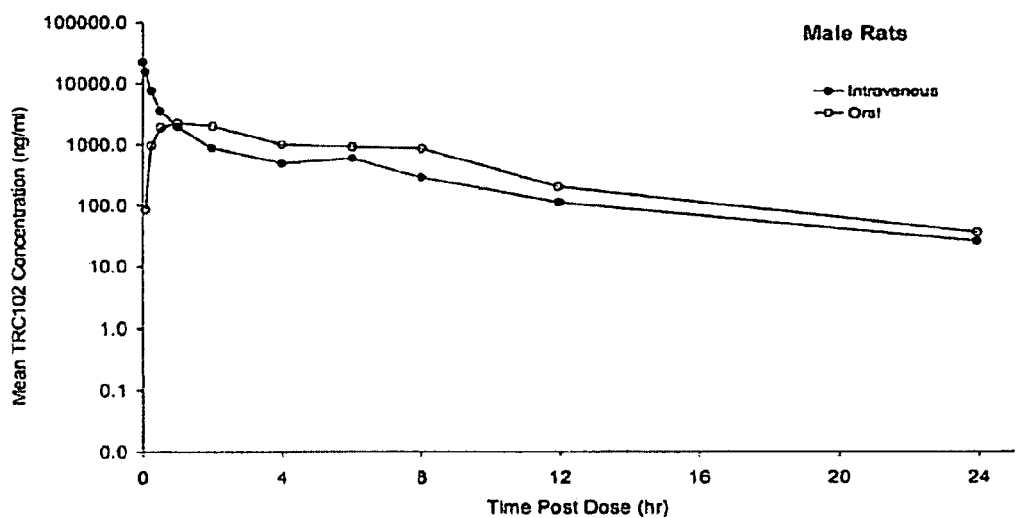

Fig. 3  Mean TRC102 Concentration in Plasma from Female Sprague Dawley Rats at Different Time Points After a Single Bolus Dosing of TRC102 via Intravenous and Oral Administration at 20 mg/kg Body Weight

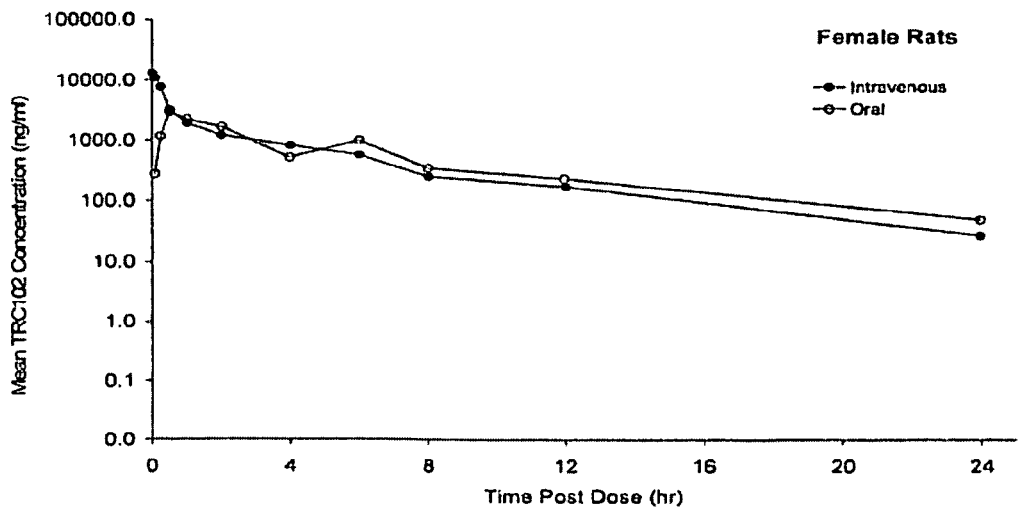

AP Sites Detected in H460 Cells After Treatment with Pemetrexed and TRC102

TRC102 Bound AP Sites are Refractory to the Repair by AP Endonuclease

A. Schematic diagram indicate the preparation of a position specific oligonucleotide substrates containing an AP site or an TRC102 bound AP site.
B. APE has the ability to cleave the AP site but not the TRC102 bound AP site, indicating that TRC102 bound AP site is refractory to the repair by APE.

TRC102 Enhances Anti-tumor Effect of Pemetrexed in Nude Mice Carrying Human Tumors $*P < 0.05$

ANTIFOLATE AGENT COMBINATIONS IN THE TREATMENT OF CANCER

RELATED APPLICATIONS

The present application claims priority to the U.S. Provisional Patent Application Ser. No. 60/877,836, filed on Dec. 29, 2006, by Theuer et al., and entitled "ANTIMETABOLITE AGENT COMBINATIONS IN THE TREATMENT OF CANCER," the U.S. Provisional Patent Application Ser. No. 60/883,266, filed on Jan. 3, 2007, by Theuer et al., and entitled "ANTIMETABOLITE AGENT COMBINATIONS IN THE TREATMENT OF CANCER," and the U.S. Provisional Patent Application Ser. No. 60/883,959, filed on Jan. 8, 2007, by Theuer et al., and entitled "ANTIMETABOLITE AGENT p COMBINATIONS IN THE TREATMENT OF CANCER," all of which are incorporated by reference herein in their entirety, including any drawings.

FIELD OF THE INVENTION

The present invention relates generally to compounds having various utilities including uses for research, diagnostics, and therapy. More specifically, described and provided herein compositions comprising methoxyamine and an antimetabolite anticancer agent, and methods of treating certain cancers by administering these compositions.

BACKGROUND

Cancer is a worldwide problem. As such, finding novel compositions and methods for the treatment of cancer is of vital interest. The treatment of cancer falls into three general categories: chemotherapy, radiation therapy and surgery. Often, therapies are combined since a combination of therapies often increases the probability the cancer will be eradicated as compared to treatment strategies utilizing a single therapy. Typically, the surgical excision of large tumor masses is followed by chemotherapy and/or radiation therapy.

Chemotherapeutic agents can work in a number of ways. For example, chemotherapeutics can work by interfering with cell cycle progression or by generating DNA strand breaks. If the cancer cell is not able to overcome the cell cycle blockage or cell injury caused by the therapeutic compound, the cell will often die via apoptotic mechanisms. The use of a single chemotherapeutic agent in the treatment of cancer, with or without surgery or radiation, has several disadvantages. Commonly, cancer cells develop resistance to the chemotherapeutic agent. Such resistance results either in the requirement for higher dosages of the drug and/or the renewed spread of the cancer. Chemotherapeutic agents can be toxic to the patient. Therefore, there is a practical upper limit to the amount that a patient can receive. However, if a second agent can be developed to inhibit the pathway causing resistance, cancer cells may become susceptible to the effects of the chemotherapeutic agent.

The design of a drug to overcome resistance to the chemotherapeutic treatment of cancer should be approached with the goals of 1) finding a combination that reverses resistance and not merely improves the activity of the chemotherapeutic with respect to activity on the tumor, and 2) finding a second drug that does not potentiate the toxic effects of the first chemotherapeutic agent. These conditions require a great deal of empirical testing of agents known to have anticancer properties with agents that either may have anticancer properties, or that may augment the first agent in other ways. Unfortunately, such approaches have thus far proven largely unsuccessful for combinations of many anticancer agents.

Therefore, there exist insufficient therapies that reverse resistance to chemotherapy for the treatment of cancer.

SUMMARY OF THE INVENTION

The inventions described and claimed herein have many attributes and embodiments including, but not limited to, those set forth or described or referenced in this Summary of the Invention. The inventions described and claimed herein are not limited to or by the features or embodiments identified in this Summary of the Invention, which is included for purposes of illustration only and not restriction.

These and other aspects and embodiments of the inventions described and claimed herein will be apparent from and throughout the application and claims, all of which shall be considered to be a part of the written description thereof.

Disclosed herein are compositions and methods useful in the treatment of certain cancers. In part, this application is based on the heretofore unknown recognition that certain molecules that target abasic lesions or AP (apurinic/apyrimidinic) sites in DNA improve, augment, or potentiate the efficacy of antimetabolite anticancer agents. In other embodiments, an inhibitor of the base excision pathway, such as methoxyamine, is combined with an antimetabolite anticancer agent. An antimetabolite anticancer agent is a chemotherapeutic with a similar structure to a substance (a metabolite) required for normal biochemical reactions, yet different enough to interfere with the normal functions of cells, including cell division. Antifolates are a preferred class of antimetabolite agents. An antifolate anticancer agent is a chemotherapeutic with a similar structure to folic acid, yet different enough to block the activity of folic acid and disrupt folate-dependent mechanisms necessary for cell replication. These antifolate anticancer agents include pemetrexed, capecitabine, edatrexate, methotrexate, lometrexol, nolatrexed, ralitrexed, PT523, and trimetrexate. The use of any antifolate anticancer agent in combination with a BER (base excision repair) inhibitor is contemplated.

In one aspect, the instant invention is based on the previously unknown recognition that certain molecules, such as methoxyamine, that target AP sites are completely orally bioavailable and maintain minimal effective concentrations when given once or twice daily by oral administration. Anticancer agents are typically administered as an intravenous L bolus, as they are rarely well absorbed from the gastrointestinal tract. Intravenous dosing has disadvantages. First, the intravenous injection of chemotherapy requires treatment in a physician's office or hospital. Second, intravenous therapy is typically given as a bolus, which results in a very high but transient drug exposure. Some anticancer agents may be most active following sustained exposure that can be achieved with repeated oral doses. This is particularly true of agents that inhibit resistance mechanisms to chemotherapy drugs, where prolonged inhibition of resistance pathways may be necessary for a desired beneficial effect. Prolonged drug exposure may be accomplished using continuous intravenous administration. However, administration of anticancer agents as continuous infusions requires a complicated drug infusion apparatus and intravenous catheterization. Oral administration obviates the need for continuous intravenous infusion and is a route of administration preferred by patients. However, to our knowledge, inhibitors of BER that reverse resistance to chemotherapy and have nearly complete oral bioavailability as provided herein have not been developed to date.

Pemetrexed is a multitargeted antifolate that acts in a manner that is mechanistically different from 5-FU and other early generation antimetabolites. Pemetrexed is unique in that it is a pyrrolopyrimidine antifolate analog that is metabolized intracellularly to higher polyglutamate forms by folylpolyglutamate synthetase (FPGS). The pentaglutamate form is the predominant intracellular species and pemetrexed polyglutamates are approximately 60-fold more potent than the parent monoglutamate compound; pemetrexed polyglutamates also exhibit prolonged cellular retentions. Hence, pharmacologic effects of pemetrexed persist for many days following intravenous bolus administration.

Pemetrexed inhibits thymidylate synthase (TS), dihydrofolate reductase (DHFR) and glycinamide ribonucleotide formyltransferase (GARFT), all folate-dependent enzymes involved in the de novo biosynthesis of thymidine and purine nucleotides. In contrast, 5-FU and other early generation antimetabolites primarily inhibit TS only. The precise mechanism by which pemetrexed causes cell death is still not resolved but involves more than TS inhibition. Hence, while in a heterogeneous nonselected human colon cancer cell line panel, the best predictor for sensitivity to 5FU was TS activity, multiple sensitivity determinants were of importance for pemetrexed, including FPGS activity and TS enzyme kinetics (van Triest B, Pinedo H M, van Hensbergen Y. Thymidylate synthase level as the main predictor parameter for sensitivity to 5-FU, but not for Folate-based Thymidylate Synthase Inhibitors, in 13 Nonselected Colon Cancer Cell Lines. Clin. Cancer. Res. 1999; 5:643-54). Further study confirmed that the sensitivity of gastrointestinal cell lines to pemetrexed could not be predicted by the expression of TS (Kim J H, Lee K W, Jung Y et al. Cytotoxic effects of pemetrexed in gastric cancer cells. Cancer Sci. 2005; 96:365-71).

The unique pharmacologic activity of pemetrexed is made evident by in vitro study of activity on multiple cancer cell lines as compared to 5-FU. In a series of 13 colon cancer cell lines, for example, pemetrexed was from 18 to 627-times more potent than 5-FU (van Triest et al, 1999). This unique pharmacology and the fact that pemetrexed is believed to have multiple mechanisms of action that are not completely understood makes it difficult to know how effective it might be when combined with other particular anticancer agents for the treatment of specific cancers.

One aspect of the instant invention is the finding of an unexpected improvement in the treatment of cancers by the combined administration of methoxyamine with an antifolate compound. Thus, one embodiment described herein is directed to methods comprising providing i) a patient diagnosed with cancer, ii) a first formulation comprising an antifolate anticancer agent and iii) a second formulation comprising methoxyamine; administering the first formulation to the patient; and administering the second formulation to said patient wherein methoxyamine can be administered in an amount sufficient to enhance or increase the effect (i.e. potentiate activity) of the antifolate anticancer agent. Any antifolate anticancer agent may be used, with the proviso that in certain embodiments the method, 5-FU is specifically excluded. In a typical embodiment, the anticancer agent can be selected from the group consisting of pemetrexed, edatrexate, methotrexate, lometrexol, nolatrexed, ralitrexed, PT523, trimetrexate, aminopterin, 5,10-Dideazatetrahydrofolic acid. (DDATHF), piritrexim, raltitrexed, GW1843 [(S)-2-[5-[(1,2-dihydro-3-methyl-1-oxobenzo[f]quinazolin-9-yl)methyl]amino-1-oxo-2-isoindolynl]-glutaric acid], pharmaceuticals salts thereof and any combinations. In a more typical embodiment, the anticancer agent can be selected from the group consisting of pemetrexed, edatrexate, methotrexate, lometrexol, nolatrexed, ralitrexed, PT523, trimetrexate, aminopterin, pharmaceuticals salts thereof and any combinations. In a most typical embodiment, anticancer agent can be pemetrexed and pharmaceutically acceptable salts thereof. For example, the pemetrexed can be the disodium salt. In an exemplary embodiment the pemetrexed can be the disodium salt heptahydrate.

In a typical but non-limiting embodiment the antifolate anticancer agent is pemetrexed. The methoxyamine and antifolate anticancer agent may be administered sequentially (in either order) or administered together as a formulation. The pemetrexed may, for example, be administered intravenously in a dose of between 200 and 1,000 mg/m$^2$ body surface area per day, or in a dose of between 500 and 600 mg/m$^2$ body surface area per day. In another embodiment, the ratio of methoxyamine to the antifolate anticancer agent can be between 1:5 and 1:500.

In another aspect, methoxyamine can be administered orally in an amount sufficient to sensitize the cancer without causing undue sensitization of normal tissue. In non-limiting preferred embodiments, methoxyamine is administered orally such that it has a greatly enhanced bioavailability relative to other anticancer agents administered orally. In other non-limiting preferred embodiments, methoxyamine is administered orally such that it maintains a minimum effective concentration when dosed once daily or twice daily. One way to measure oral bioavailability is to compare the levels achieved against those of intravenously administered methoxyamine. Thus in another aspect of the instant invention, methoxyamine is administered orally to obtain a bioavailability of at least 50% relative to intravenous administration, at least 60% relative to intravenous administration, at least 70% relative to intravenous administration, at least 75% relative to intravenous administration, at least 80% relative to intravenous administration, at least 85% relative to intravenous administration, at least 90% relative to intravenous administration, at least 95% relative to intravenous administration, or roughly equivalent to that of intravenous administration. It is significant to recognize that, in addition to the unexpected high degree of bioavailability achieved by oral administration as compared to intravenous administration of methoxyamine, a more desirable pK profile is obtained as compared to intravenous administration of methoxyamine. In another aspect of the instant invention, orally administered methoxyamine maintains minimum effective concentrations following once or twice daily administration due to a half life of >4 hours in plasma. This advantage permits a desirable oral dosing regimen for methoxyamine, including once or twice daily administration. While the intravenous administration of pemetrexed combined with the oral administration of methoxyamine are preferred non-limiting embodiments, other routes of administration are contemplated for each of the anticancer agents.

In another aspect of the invention, methods are provided for the treatment of certain cancers that are resistant to the treatment with one anticancer agent. Accordingly, there are also provided methods comprising:

providing i) a patient diagnosed with cancer, wherein said cancer can be resistant to treatment by pemetrexed alone, ii) a first formulation comprising an antifolate anticancer agent; and iii) a second formulation comprising methoxyamine;

administering the first formulation to the patient; and administering the second formulation to the patient wherein methoxyamine can be administered in an amount sufficient to enhance or increase the effect (i.e. potentiate toxicity) of the antifolate anticancer agent. In one embodiment, the antifolate anticancer agent can be pemetrexed. The methoxyamine and antifolate anticancer agent may be administered sequentially (in either order) or administered together as a formulation. The pemetrexed may be administered intravenously in a dose of between 200 and 1,000 mg/m$^2$ body surface area per day, or in a dose of between 500 and 600 mg/m$^2$ body surface area per day. The ratio of pemetrexed to methoxyamine may be between 1:5 and 1:500. In another embodiment, the amount of methoxyamine can be administered orally in an amount sufficient to sensitize the cancer without causing undue sensitization of normal tissue. In another embodiment, the amount of methoxyamine can be administered orally either once daily or twice daily in an amount sufficient to sensitize the cancer without causing undue sensitization of normal tissue. While the oral administration of methoxyamine is an unexpectedly preferred route of administration, other types of administration are possible.

Another embodiment is directed to a method of treating cancer by providing a first and second formulation wherein said first formulation comprises an antifolate and the second formulation comprises an orally administered methoxyamine. The first formulation comprising an antifolate may be administered by conventional routes of administration, including intravenously. A non-limiting preferred antifolate is pemetrexed. Accordingly, in one embodiment the antifolate is pemetrexed and the second formulation comprising methoxyamine is administered orally in an amount that is synergistically effective as compared to a treatment with pemetrexed alone.

In another aspect, the method may be used to treat cancers that are resistant to pemetrexed alone. According to these embodiments, pemetrexed is administered in an amount that reverses resistance (and is therefore synergistic) to the antifolate alone. Thus in one embodiment methoxyamine is administered orally in an amount effective to enhance or increase the toxicity of the pemetrexed and overcome the resistance of the cancer to treatment with pemetrexed. For example, the effectiveness of pemetrexed to treat cancer may be reduced due to the development of resistance during the treatment cycle. The administration of methoxyamine can circumvent the developed resistance providing a greater than additive effect to treatment of the cancer with either methoxyamine or pemetrexed alone.

Also provided are methods comprising:
providing i) a patient diagnosed with cancer, wherein the cancer can be selected from the group consisting of carcinomas, melanomas, sarcomas, lymphomas, leukemias, astrocytomas, gliomas, malignant melanomas, chronic lymphocytic leukemia, lung cancers, colorectal cancers, ovarian cancers, pancreatic cancers, renal cancers, endometrial cancers, gastric cancers, liver cancers, head and neck cancers, and breast cancers, and wherein the cancer can be resistant to treatment with pemetrexed alone, ii) a first formulation comprising an antifolate anticancer agent and iii) a second formulation comprising methoxyamine;
administering the first formulation to said patient; and
administering the second formulation to said patient wherein methoxyamine can be administered in an amount sufficient to enhance or increase the effect of the antifolate anticancer agent. The methoxyamine and antifolate anticancer agent may be administered sequentially or administered together as a formulation. For example, the methoxyamine can be administered first and then the antifolate anticancer agent can be administered last or the antifolate anticancer agent can be administered first and the methoxyamine can be administered last.

In a typical embodiment, the antifolate anticancer agent can be pemetrexed. The pemetrexed may be administered intravenously in a dose of between 200 and 1,000 mg/m$^2$ body surface area per day, or in a dose of between 500 and 600 mg/m$^2$ body surface area per day. The ratio of pemetrexed to methoxyamine may be between 1:5 and 1:500. In another embodiment, the amount of methoxyamine can be administered orally in an amount sufficient to cause the cancer cells to be susceptible to treatment with the anticancer agent (i.e. sensitize) without causing undue damage to normal cells. In another embodiment, the amount of methoxyamine can be administered orally either once or twice daily in an amount sufficient to sensitize the cancer without causing undue sensitization of normal tissue.

Another embodiment can be a formulation comprising methoxyamine and an antifolate anticancer agent, wherein methoxyamine can be administered in an amount sufficient to potentiate toxicity of the antifolate anticancer agent. Preferably, the antifolate anticancer agent is pemetrexed.

In another embodiment, the ratio of methoxyamine to the antifolate anticancer agent can be between 1:5 and 1:500 in any of the methods described above.

In another embodiment, a second anticancer agent can be administered prior to or after treatment with methoxyamine and the antifolate anticancer agent in any of the methods described above.

In another embodiment, a method is described for treating cancer in a patient diagnosed with cancer comprising administering an antimetabolite anticancer agent to the patient, having the following improvement: administering methoxyamine to the patient in an amount sufficient to potentiate toxicity of said antimetabolite anticancer agent. The antimetabolite anticancer agent may be an antifolate anticancer agent. The antifolate anticancer agent may be pemetrexed, and the ratio of said methoxyamine to the antifolate anticancer agent may be between 1:5 and 1:500. The cancer may be resistant to treatment with pemetrexed alone.

BRIEF DESCRIPTION OF THE DRAWINGS

FIGS. 1A-B show the effect of pemetrexed and MX on DNA strand breaks using the alkaline (FIG. 1A) and neutral (FIG. 1B) comet assay.

FIGS. 1C-D show a comparison of comet tail length between cells treated with pemetrexed alone or MX alone, and pemetrexed plus MX in cells subjected to the alkaline (FIG. 1C) and neutral (FIG. 1D) Comet assays.

FIG. 2 is a graph showing mean MX concentration in plasma from male Sprague-Dawley rats at different time points after a single bolus dosing of MX via intravenous and oral administration at 20 mg/kg body weight.

FIG. 3 is a graph showing mean MX concentration in plasma from female Sprague-Dawley rats at different time points after a single bolus dosing of MX via intravenous and oral administration at 20 mg/kg body weight.

DETAILED DESCRIPTION

Figure 4A:
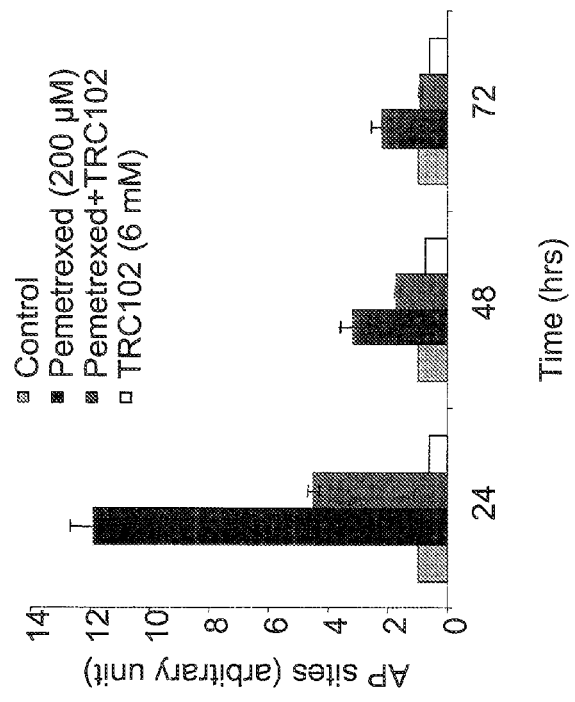
FIG. 4A is a graph showing the relative amount of AP sites detected in H460 cells 24 hours after treatment with pemetrexed and MX.

Certain embodiments of the invention generally relate to novel compositions comprising methoxyamine and an antifolate anticancer agent, and treatment of certain cancers using these compositions.

Definitions

Unless indicated otherwise, the following terms have the following meanings when used herein and in the appended claims. Those terms that are not defined below or elsewhere in the specification shall have their art-recognized meaning.

The term "agent" and "drug" are used herein, for purposes of the specification and claims, to mean chemical compounds, mixtures of chemical compounds, biological macromolecules, or extracts made from biological materials such as bacteria, plants, fungi, or animal particularly mammalian) cells or tissues that are suspected of having therapeutic properties. The agent or drug may be purified, substantially purified or partially purified.

The term "antimetabolite" is used herein, for purposes of the specification and claims, to mean a chemotherapeutic with a similar structure to a substance (a metabolite e.g. nucleoside) required for normal biochemical reactions, yet different enough to interfere with the normal functions of cells, including cell division.

The term "antifolate" is used herein, for purposes of the specification and claims, to mean a chemotherapeutic with a similar structure to folic acid, yet different enough to block the activity of folic acid and disrupt folate-dependent mechanisms necessary for cell replication. As use herein, antifolates are one class of antimetabolites.

The term "antineoplastic" is used herein, for purposes of the specification and claims, to mean a chemotherapeutic intended to inhibit or prevent the maturation and proliferation of neoplasms (tumors) that may become malignant, by targeting the DNA.

The term "staining" is used herein, for purposes of the specification and claims, to mean any number of processes known to those in the field that are used to better visualize, distinguish or identify a specific component(s) and/or feature(s) of a cell or cells.

The term "in operable combination", "in operable order" and "operably linked" is used herein, for purposes of the specification and claims, to mean the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "antigen" is used herein, for purposes of the specification and claims, to mean a protein, glycoprotein, lipoprotein, lipid or other substance that is reactive with an antibody specific for a portion of the molecule.

The term "morphology" is used herein, for purposes of the specification and claims, to mean the visual appearance of a cell or organism when viewed with the eye, a light microscope, a confocal microscope or an electron microscope, as appropriate.

The term "subject," "individual," and "patient" are used herein, for purposes of the specification and claims, to mean a human or other animal, such as farm animals or laboratory animals (e.g., guinea pig or mice) capable of having cell cycle (influenced) determined diseases, either naturally occurring or induced, including but not limited to cancer.

The term "reverses resistance" means that the use of a second agent in combination with a primary chemotherapeutic is able to produce a significant decrease in tumor volume at a level of statistical significance (e.g., $p<0.05$) when compared to tumor volume of untreated tumor in the circumstance where the primary chemotherapeutic alone is unable to produce a statistically significant decrease in tumor volume compared to tumor volume of untreated tumor. This generally applies to tumor volume measurements made at a time when the untreated tumor is growing log rhythmically.

The term "potentiate" as used herein means to enhance or increase the beneficial activity or efficacy of the anticancer agent over that which would be expected from the anticancer agent alone or the potentiating agent alone.

The term "sensitize" as used herein means to alter cancer cells or tumor cells in a way that allows for more effective treatment of the associated neoplastic disease with an anticancer agent or radiation therapy. In some embodiments, normal cells are not affected to an extent that causes the normal cells to be unduly injured by the chemotherapy or radiation therapy.

The term "synergistic effect" as used herein means the combined effect of two or more anticancer agents or chemotherapy drugs can be greater than the sum of the separate effects of the anticancer agents or chemotherapy drugs alone. For example, the combined effect of a BER inhibitor, such as methoxyamine, and an anticancer agent, such as pemetrexed, can be greater than the sum of the separate effects of methoxyamine and pemetrexed alone.

The term "therapeutically effective amount" means the amount of the subject compound that will elicit a desired response, for example, a biological or medical response of a tissue, system, animal, or human that is sought, for example, by a researcher, veterinarian, medical doctor, or other clinician.

The term "wild type" (wt) cell or cell line is used herein, for purposes of the specification and claims, to mean a cell or cell line that retains the characteristics normally associated with that type of cell or cell line for the physiological process or morphological characteristic that is being examined. It is permissible for the cell or cell line to have non-wild type characteristics for physiological process or morphological characteristics that are not being examined as long as they do not appreciably affect the process or characteristic being examined.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D- glucamine, tris(hydroxymethyl)methylamine, $C_1$-$C_7$ alkylamine, cyclohexylamine, triethanolamine, ethylenediamine, and salts with amino acids such as arginine, lysine, and the like.

Injury to DNA is minimized by enzymes that recognize errors, remove them, and replace the damaged DNA with corrected nucleotides. DNA damage occurs when a single-strand break is introduced, a base is removed leaving its former partner unpaired, a base is covalently modified, a base is converted into another that is not appropriately paired with the partner base, or a covalent link is introduced between bases on opposite strands. Excision repair systems remove the mispaired or damaged base from the DNA strand and then synthesize new DNA to replace it. Base excision repair (BER) is initiated during replication of DNA and allows for correction of damaged bases/mispaired bases prior to completion of replication.

Figure 7:
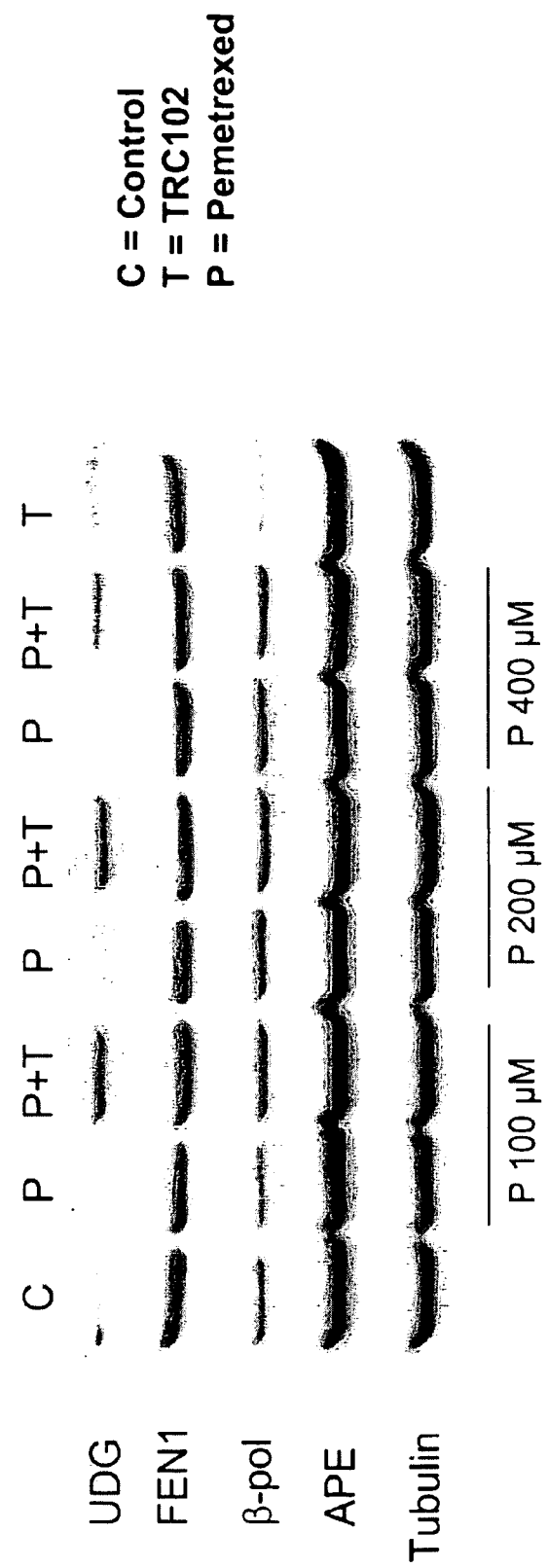
FIG. 7 shows the effect of Pemetrexed and MX in combination on BER protein levels in H460 Cells.

Base excision repair (BER) is initiated by a DNA glycosylase that removes N-glycosidic (base-sugar) bonds, liberating the damaged base and generating an abasic site (e.g. an apurinic or apyrimidinic (AP) site). An apurinic or apyrimidinic (AP) site results from the loss of a purine or pyrimidine residue, respectively, from DNA (deoxyribonucleic acid). Uracil residues can form from the spontaneous deamination of cytosine and can lead to a C→T transition if unrepaired. There is also a glycosylase that recognizes and excises hypoxanthine, the deamination product of adenine. Other glycosylases remove alkylated bases (such as 3-methyladenine, 3-methylguanine, and 7-methylguanine), ring-opened purines, oxidatively damaged bases, and in some organisms, UV photodimers. Uracil DNA glycosylase (UDG) is an example of a DNA glycosylase. The BER protein levels of UDG are affected by treatment of a combination of pemetrexed and MX (FIG. 7).

The AP site is further processed by a 5'-3' endonuclease (AP endonuclease (APE)) that incises the phosphodiester bond on both sides of the damaged purine or pyrimidine base. The AP endonucleases introduce chain breaks by cleaving the phosphodiester bonds at the AP sites.

PARP aids in processing of DNA strand breaks induced during BER. PARP is a DNA nick surveillance protein that binds weakly to BER intermediates when single-nucleotide BER proceeds normally to completion. In contrast, when single nucleotide BER is stalled by a block in the excision step, PARP binds strongly to the BER intermediate, along with AP endonuclease (APE), DNA pol β, and FEN-1.

In mammalian cells, the 5'-deoxyribose sugar phosphate is removed by the intrinsic AP lyase (dRP) activity of DNA polymerase β (pol β). DNA polymerase enzyme also fills the gaps with new nucleotides.

Finally, DNA ligase covalently links the 3' end of the new material to the old material. Thus, the wild-type sequence is restored.

Topoisomerases I and II are also involved in DNA repair, as they recognize spontaneous AP sites and form stable cleavable complexes. Topoisomerase II inhibitors promote DNA cleavage and other chromosomal aberrations, including sister chromatid exchanges.

Some embodiments as described herein can be directed to methods comprising:
providing i) a patient diagnosed with cancer, ii) a first formulation comprising an antifolate anticancer agent and iii) a second formulation comprising methoxyamine;
administering the first formulation to the patient; and administering the second formulation to said patient wherein methoxyamine can be administered in an amount sufficient to enhance or increase the effect of the antifolate anticancer agent. Any antifolate anticancer agent may be used, with the proviso that in certain embodiments the method, 5-FU is specifically excluded.

In a typical embodiment, the anticancer agent can be selected from the group consisting of pemetrexed, capecitabine, edatrexate, methotrexate, lometrexol, nolatrexed, ralitrexed, PT523, trimetrexate, aminopterin, 5,10-Dideazatetrahydrofolic acid. (DDATHF), piritrexim, raltitrexed, GW1843 [(S)-2-[5-[(1,2-dihydro-3-methyl-1-oxobenzo[f]quinazolin-9-yl)methyl]amino-1-oxo-2-isoindolynl]-glutaric acid], pharmaceuticals salts thereof and any combinations. In a more typical embodiment, the anticancer agent can be selected from the group consisting of pemetrexed, capecitabine, edatrexate, methotrexate, lometrexol, nolatrexed, ralitrexed, PT523, trimetrexate, aminopterin, pharmaceuticals salts thereof and any combinations. In a most typical embodiment, anticancer agent can be pemetrexed and pharmaceutically acceptable salts thereof. For example, the pemetrexed can be the disodium salt. In an exemplary embodiment the pemetrexed can be the disodium salt heptahydrate.

In certain embodiments, the present invention contemplates the use of an anticancer agent that induces the formation of AP sites, and a BER inhibitor In a typical embodiment, the anticancer agent can be selected from the group consisting of pemetrexed, capecitabine, edatrexate, methotrexate, lometrexol, nolatrexed, ralitrexed, PT523, trimetrexate, aminopterin, 5,10-Dideazatetrahydrofolic acid. (DDATHF), piritrexim, raltitrexed, GW1843 [(S)-2-[5-[(1,2-dihydro-3-methyl-1-oxobenzo[/]quinazolin-9-yl)methyl]amino-1-oxo-2-isoindolynl]-glutaric acid], pharmaceutical salts thereof and any combinations. In a more typical embodiment, the anticancer agent can be selected from the group consisting of pemetrexed, capecitabine, edatrexate, methotrexate, lometrexol, nolatrexed, ralitrexed, PT523, trimetrexate, aminopterin, pharmaceuticals salts thereof and any combinations. In a most typical embodiment, anticancer agent can be pemetrexed and pharmaceutically acceptable salts thereof. For example, the pemetrexed can be the disodium salt. In an exemplary embodiment the pemetrexed can be the disodium salt heptahydrate.

In a typical embodiment, the BER inhibitor can be selected from the group consisting of methoxy amine, etoposide (VP-16, VP-16-123), meso-4,4'-(2,3-butanediyl)-bis-(2,6-piperazinedione) (ICRF-193, a bisdioxopiperazine), doxorubicin (DOX), amsacrine (4',9-acridinylaminomethanesulfon-m-anisidide; mAMSA), pazelliptine, nalidixic acid, oxolinic acid, novobiocin, coumermycin A1, fostriecin, teniposide, mitoxantrone, daunorubicin, N-[2-dimethylamino)ethyl] acridine-4-carboxamide (DACA), merbarone, quinacrine, ellipticines, epipodophyllotoxins, ethidium bromide, epirubicin, pirarubicin, 3'-deamino-3'-morpholino-13-deoxo-10-hydroxy caminomycin; 2'',3''-bis pentafluorophenoxyacetyl-4',6'-ethylidene-beta-D glucoside of 4'-phosphate-4'-dimethylepipodophyollotoxin 2N-methyl glucamine salt (F11782; a fluorinated lipophilic epipodophylloid), adriamycin, actinomycin D, anthracyclines (such as 9-aminoanthracycline), pyrazoloacridine (PZA), camptothecin, topotecan pharmaceutical salts and solvants thereof and any combinations. In a more typical embodiment, the BER inhibitor can be selected from the group consisting of methoxyamine (MX), N-ethylmaleimide, $O^6$-benzylguanine, pharmaceutically acceptable salts thereof and any combinations. In a most typical embodiment, the BER inhibitor can be methoxyamine (MX) or salts thereof.

In one embodiment, the BER inhibitor can be compounds having structures of formula I:

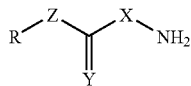

Formula I wherein X is O or NH,
Y is O, S, or NH,
Z is absent or represents O, S, or NH,
R represents a hydrogen or a hydrocarbon moiety, and pharmaceutically acceptable salts thereof.

In some embodiments, a BER inhibitor can be used to treat a patient or subject having a neoplastic disease. For example, the neoplastic disease can be a cancer selected from the group consisting of carcinomas, melanomas, sarcomas, lymphomas, leukemias, astrocytomas, gliomas, malignant melanomas, chronic lymphocytic leukemia, lung cancers, prostate cancer, colorectal cancers, ovarian cancers, pancreatic cancers, renal cancers, endometrial cancers, gastric cancers, liver cancers, head and neck cancers.

In some embodiments, a BER inhibitor can be used to treat a patient or individual having a neoplastic disease that is being treated with an anticancer agent.

In a typical embodiment, the BER inhibitor can be selected from the group consisting methoxy amine, etoposide (VP-16, VP-16-123), meso-4,4'-(2,3-butanediyl)-bis-(2,6-piperazinedione) (ICRF-193, a bisdioxopiperazine), doxorubicin (DOX), amsacrine (4',9-acridinylaminomethanesulfon-m-anisidide; mAMSA), pazelliptine, nalidixic acid, oxolinic acid, novobiocin, coumermycin A1, fostriecin, teniposide, mitoxantrone, daunorubicin, N-[2-dimethylamino)ethyl] acridine-4-carboxamide (DACA), merbarone, quinacrine, ellipticines, epipodophyllotoxins, ethidium bromide, epirubicin, pirarubicin, 3'-deamino-3'-morpholino-13-deoxo-10-hydroxy caminomycin; 2",3"-bis pentafluorophenoxyacetyl-4',6'-ethylidene-beta-D glucoside of 4'-phosphate-4'-dimethylepipodophyollotoxin 2N-methyl glucamine salt (F11782; a fluorinated lipophilic epipodophylloid), adriamycin, actinomycin D, anthracyclines (such as 9-aminoanthracycline), pyrazoloacridine (PZA), camptothecin, topotecan pharmaceutical salts thereof and any combinations. In a more typical embodiment, the BER inhibitor can be selected from the group consisting of methoxyamine (MX), N-ethylmaleimide, $O^6$-benzylguanine, pharmaceutically acceptable salts thereof and any combinations. In a most typical embodiment, the BER inhibitor can be methoxyamine (MX) or salts thereof.

In a typical embodiment, the anticancer agent can be selected from the group consisting of pemetrexed, capecitabine, edatrexate, methotrexate, lometrexol, nolatrexed, ralitrexed, PT523, trimetrexate, aminopterin, 5,10-Dideazatetrahydrofolic acid. (DDATHF), piritrexim, raltitrexed, GW1843 [(S)-2-[5-[(1,2-dihydro-3-methyl-1-oxobenzo[f]quinazolin-9-yl)methyl]amino-1-oxo-2-isoindolynl]-glutaric acid], pharmaceuticals salts thereof and any combinations. In a more typical embodiment, the anticancer agent can be selected from the group consisting of pemetrexed, capecitabine, edatrexate, methotrexate, lometrexol, nolatrexed, ralitrexed, PT523, trimetrexate, aminopterin, pharmaceuticals salts thereof and any combinations. In a most typical embodiment, anticancer agent can be pemetrexed and pharmaceutically acceptable salts and solvates thereof. For example, the pemetrexed can be the disodium salt. In an exemplary embodiment the pemetrexed can be the disodium salt heptahydrate.

In some embodiments, the BER inhibitor and the anticancer agent can be administered to an individual in combination. For example, the BER inhibitor and the anticancer agent can be administered to an individual together in an parenteral formulation. Alternatively, the BER inhibitor and the anticancer agent can be administered to an individual together in a oral formulation, such as a solid dosage formulation.

In some embodiments, the BER inhibitor and the anticancer agent can be administered to an individual sequentially, where the individual is first given the anticancer agent and then given the BER inhibitor. For example, the individual can be given the anticancer agent in a parenteral formulation, such as an intravenous formulation, or an oral formulation, such as a solid dosage formulation and then given the BER inhibitor in a parenteral formulation, such as an intravenous formulation, or an oral formulation, such as a solid dosage formulation.

Alternatively, in some embodiments, the BER inhibitor and the anticancer agent can be administered to an individual sequentially, where the individual is first given the BER inhibitor and then given the anticancer agent. For example, the individual can be given the BER inhibitor in a parenteral formulation, such as an intravenous formulation, or an oral formulation, such as a solid dosage formulation and then given the anticancer agent in a parenteral formulation, such as an intravenous formulation, or an oral formulation, such as a solid dosage formulation.

In some embodiments, the anticancer agent and the BER inhibitor can create an anticancer effect greater than that of the separate anticancer effects of the individual agents. For example, the combined anticancer effect of the anticancer agent and the BER inhibitor can be greater than the added anticancer effect of the anticancer agent and the BER inhibitor when used individually.

Thus, compounds useful as BER inhibitors such as methoxyamine (MX), N-ethylmaleimide, $O^6$-benzylguanine, and compounds having structures of formula I:

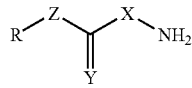

Formula I wherein X is O or NH,
Y is O, S, or NH,
Z is absent or represents O, S, or NH, and
R represents a hydrogen or a hydrocarbon moiety,
and pharmaceutically acceptable salts thereof.

In single-nucleotide BER, the deoxyribose phosphate (dRP) in the abasic site is removed by the lyase activity of DNA pol β. Compounds such as methoxyamine react with the aldehyde of an abasic site, making it refractory to the β-elimination step of the dRP lyase mechanism, thus blocking single-nucleotide BER.

In some embodiments, suitable compounds can prevent the substrate of AP endonuclease from being susceptible to cleavage. Anticancer agents may act by binding to AP sites and preventing APE-mediated cleavage of phosphodiester bonds. Other compounds that may bind to AP sites and prevent APE-mediated cleavage of phosphodiester bonds include O-benzylhydroxylamine; ethyl aminooxyacetate; aminooxyacetic acid; ethyl aminooxyacetate; $H_2N$—

OCHMeCO$_2$H; carboxymethoxyamine; aminooxyacetic acid; HN=C(NH$_2$)SCH$_2$CH$_2$ONH$_2$; H$_2$N—O(CH$_2$)$_3$SC(NH$_2$)=NH; MeOC(O)CH(NH$_2$)CH$_2$O—NH$_2$; H$_2$NOCH$_2$CH(NH$_2$)CO$_2$H; canaline; H$_2$N—O(CH$_2$)$_4$O—NH$_2$; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; H$_2$C=CHCH$_2$O—NH$_2$; H$_2$N—O(CH$_2$)$_4$O—NH$_2$; H$_3$C(CH$_2$)$_{15}$O—NH$_2$, 2,2'-(1,2-ethanediyl)bis(3-aminooxy)butenedioic acid dimethyl diethyl ester; compounds having any of the following structures:

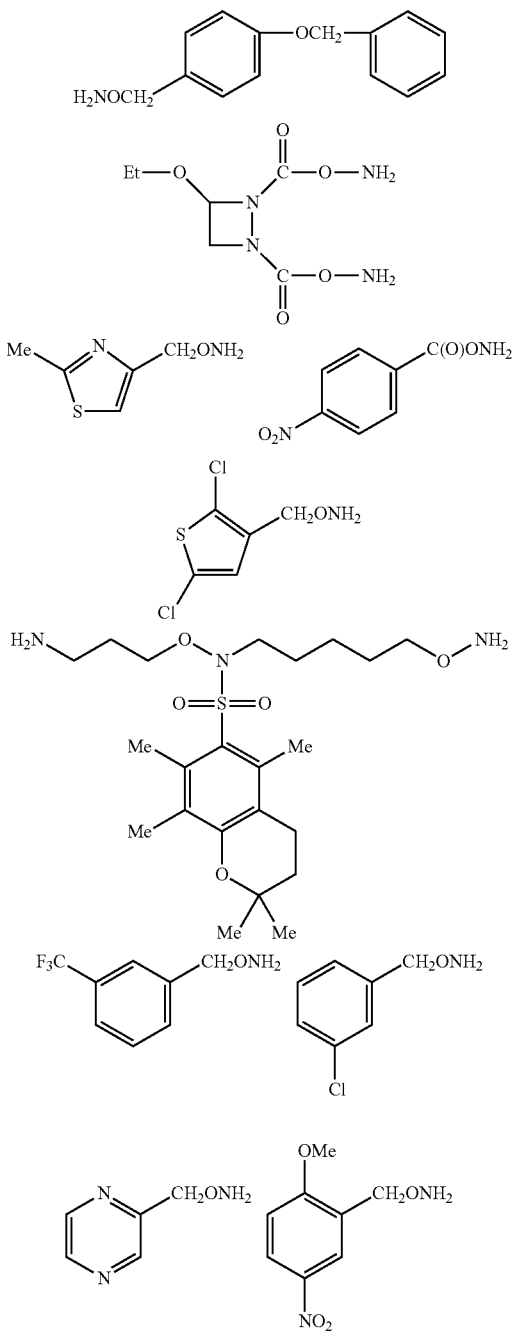

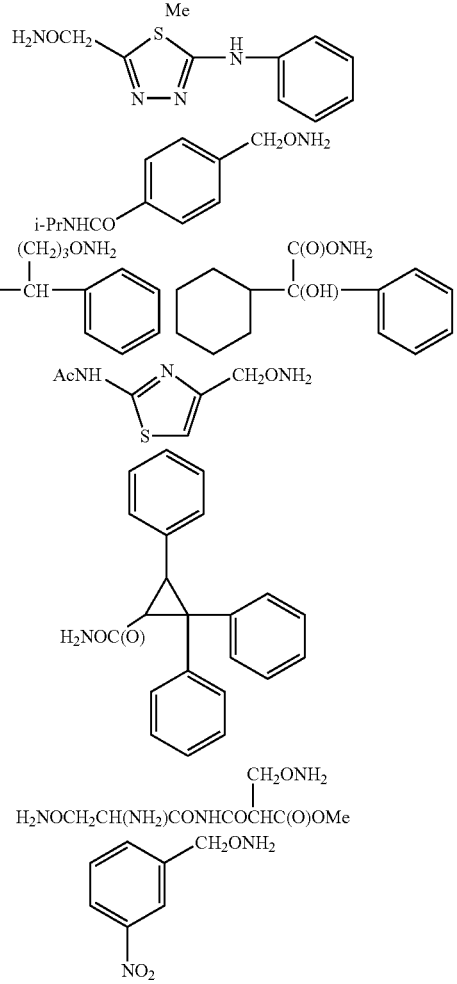

and pharmaceutically acceptable salts of any of these compounds.

Compounds useful as BER inhibitors include PARP inhibitors, such as 4-amino-1,8-naphthalimide (ANI), PD128763, 3-AB, 6-AN, and 8-hydroxy-2-methyl-quinazolin-4-[$^3$H]one (NU-1025).

Compounds useful as BER inhibitors include DNA polymerase inhibitors (e.g., DNA polymerase β, γ or ε), such as prunasin, aphidicolin, 2',3'-dideoxycytidine triphosphate (ddCTP), 2',3'-dideoxythymidine triphosphate (ddTTP), 2',3'-dideoxyadenosine triphosphate (ddATP), 2',3'-dideoxyguanosine triphosphate (ddGTP), 1-beta-D-arabinofuranosylcytosine (Ara-C), caffeine, arabinocytidine, and bleomycin.

Compounds useful as BER inhibitors include DNA ligase inhibitors (e.g., DNA ligase I, II, or III), such as ursolic and oleanolic acids, aleuritolic acid, protolichesterinic acid, swertifrancheside, fulvoplumierin, fagaronine chloride, and bleomycin. XRCC1 is the protein partner of DNA ligase III, and inhibitors of XRCC1, such as 3-AB, are useful as BER inhibitors as well.

Topoisomerase II inhibitors induce DNA cleavage and other chromosomal aberrations, including sister chromatid exchanges. Compounds useful as BER inhibitors also include topoisomerase II inhibitors, such as etoposide (VP-16, VP-16-123), meso-4,4'-(2,3-butanediyl)-bis-(2,6-piperazinedione) (ICRF-193, a bisdioxopiperazine), doxorubicin (DOX), L amsacrine (4',9-acridinylaminomethanesulfon-m-anisidide; mAMSA), pazelliptine, nalidixic acid, oxolinic acid, novobiocin, coumermycin A1, fostriecin, teniposide, mitoxantrone, daunorubicin, N-[2-dimethylamino)ethyl] acridine-4-carboxamide (DACA), merbarone, quinacrine, ellipticines, epipodophyllotoxins, ethidium bromide, epirubicin, pirarubicin, 3'-deamino-3'-morpholino-13-deoxo-10-hydroxy caminomycin; 2",3"-bis pentafluorophenoxyacetyl-4',6'-ethylidene-beta-D glucoside of 4'-phosphate-4'-dimethylepipodophyollotoxin 2N-methyl glucamine salt (F11782; a fluorinated lipophilic epipodophylloid), adriamycin, actinomycin D, anthracyclines (such as 9-aminoanthracycline), and pyrazoloacridine (PZA). Topoisomerase I inhibitors, such as camptothecin and topotecan can also be used as BER inhibitors.

In some embodiments, other enzyme inhibitors, whether known in the art or hereafter identified, as well as inhibitors of other elements of the BER pathway, such as DNA alkyltransferase, may be employed in compositions and methods without departing from the scope and spirit of the present embodiments.

In certain embodiments, the present invention contemplates the use of an anticancer agent, such as pemetrexed, that induces the formation of AP sites and a BER inhibitor (other than a topoisomerase inhibitor), such as methoxyamine.

In a typical embodiment, the anticancer agent can be selected from the group consisting of pemetrexed, capecitabine, edatrexate, methotrexate, lometrexol, nolatrexed, ralitrexed, PT523, and trimetrexate. In a more typical embodiment, the anticancer agent can be pemetrexed and pharmaceutically acceptable salts thereof. For example, the pemetrexed can be the disodium salt. In an exemplary embodiment the pemetrexed can be the disodium salt heptahydrate.

In some embodiments, the anticancer agent can be administered in a dose of from about 25 mg/m$^2$ to about 5,000 mg/m$^2$ body surface area. For example, the dose can be from about 25 mg/m$^2$ to about 200 mg/m$^2$ body surface area; the dose can be from about 150 mg/m$^2$ to about 500 mg/m$^2$ body surface area; the dose can be from about 400 mg/m$^2$ to about 1000 mg/m$^2$ body surface area; the dose can be from about 900 mg/m$^2$ to about 5,000 mg/m$^2$ body surface area; the dose can be from about 200 mg/m$^2$ to about 1,000 mg/m$^2$ body surface area; or the dose can be from about 500 mg/m$^2$ to about 600 mg/m$^2$ body surface area. Antifolates are a non limiting preferred class of anticancer agents. In some embodiments, the anticancer agent can be selected from the group consisting of pemetrexed, capecitabine, edatrexate, methotrexate, lometrexol, nolatrexed, ralitrexed, PT523, and trimetrexate. In a more typical embodiment, the anticancer agent can be pemetrexed and pharmaceutically acceptable salts thereof. For example, the pemetrexed can be the disodium salt. In an exemplary embodiment the pemetrexed can be the disodium salt heptahydrate.

In some embodiments, the ratio of BER inhibitor to anticancer agent can be from about 1:2 to about 1:10000. For example, ratio of BER inhibitor to anticancer agent can be from about 1:2 to about 1:100; the ratio of BER inhibitor to anticancer agent can be from about 1:50 to about 1:500; the ratio of BER inhibitor to anticancer agent can be from about 1:450 to K about 1:10000; ratio of BER inhibitor to anticancer agent can be from about 1:5 to about 1:500; the ratio of BER inhibitor to anticancer agent can be from about 1:10 to about 1:50; the ratio of BER inhibitor to anticancer agent can be from about 1:15 to about 1:40; or the ratio of BER inhibitor to anticancer agent can be from about 1:20 to about 1:30. In a typical embodiment the BER inhibitor can be selected form the group consisting of methoxyamine (MX), N-ethylmaleimide, O$^6$-benzylguanine, pharmaceutically acceptable salts thereof and any combinations. In a more typical embodiment, the BER inhibitor can be methoxyamine (MX).

In some embodiments, a BER inhibitor is administered in an amount sufficient to enhance or increase the effect of an anticancer agent.

In a typical embodiment, the anticancer agent can be selected from the group consisting of pemetrexed, capecitabine, edatrexate, methotrexate, lometrexol, nolatrexed, ralitrexed, PT523, trimetrexate, aminopterin, 5,10-Dideazatetrahydrofolic acid. (DDATHF), piritrexim, raltitrexed, GW1843 [(S)-2-[5-[(1,2-dihydro-3-methyl-1-oxobenzo[f]quinazolin-9-yl)methyl]amino-1-oxo-2-isoindolynl]-glutaric acid], pharmaceuticals salts thereof and any combinations. In a more typical embodiment, the anticancer agent can be selected from the group consisting of pemetrexed, capecitabine, edatrexate, methotrexate, lometrexol, nolatrexed, ralitrexed, PT523, trimetrexate, aminopterin, pharmaceuticals salts thereof and any combinations. In a most typical embodiment, anticancer agent can be pemetrexed and pharmaceutically acceptable salts thereof. For example, the pemetrexed can be the disodium salt. In an exemplary embodiment the pemetrexed can be the disodium salt heptahydrate.

In a typical embodiment, the BER inhibitor can be selected from the group consisting methoxy amine, etoposide (VP-16, VP-16-123), meso-4,4'-(2,3-butanediyl)-bis-(2,6-piperazinedione) (ICRF-193, a bisdioxopiperazine), doxorubicin (DOX), amsacrine (4',9-acridinylaminomethanesulfon-m-anisidide; mAMSA), pazelliptine, nalidixic acid, oxolinic acid, novobiocin, coumermycin A1, fostriecin, teniposide, mitoxantrone, daunorubicin, N-[2-dimethylamino)ethyl] acridine-4-carboxamide (DACA), merbarone, quinacrine, ellipticines, epipodophyllotoxins, ethidium bromide, epirubicin, pirarubicin, 3'-deamino-3'-morpholino-13-deoxo-10-hydroxy caminomycin; 2",3"-bis pentafluorophenoxyacetyl-4',6'-ethylidene-beta-D glucoside of 4'-phosphate-4'-dimethylepipodophyollotoxin 2N-methyl glucamine salt (F11782; a fluorinated lipophilic epipodophylloid), adriamycin, actinomycin D, anthracyclines (such as 9-aminoanthracycline), pyrazoloacridine (PZA), camptothecin, topotecan pharmaceutical salts thereof and any combinations. In a more typical embodiment, the BER inhibitor can be selected from the group consisting of methoxyamine (MX), N-ethylmaleimide, O$^6$-benzylguanine, pharmaceutically acceptable salts thereof and any combinations. In a most typical embodiment, the BER inhibitor can be methoxyamine (MX) or salts thereof. For example, the BER inhibitor can be methoxyamine hydrochloride (MX).

In some embodiments, the ratio of BER inhibitor to anticancer agent can be from about 1:2 to about 1:10000. For example, ratio of BER inhibitor to anticancer agent can be from about 1:2 to about 1:100; ratio of BER inhibitor to anticancer agent can be from about 1:50 to about 1:500; ratio of BER inhibitor to anticancer agent can be from about 1:450 to about 1:10000; ratio of BER inhibitor to anticancer agent can be from about 1:5 to about 1:500; ratio of BER inhibitor to anticancer agent can be from about 1:10 to about 1:50; the ratio of BER inhibitor to anticancer agent can be from about 1:15 to about 1:40; or ratio of BER inhibitor to anticancer agent can be from about 1:20 to about 1:30. In a typical embodiment the BER inhibitor can be selected form the group consisting of methoxyamine (MX), N-ethylmaleimide, $O^6$-benzylguanine, pharmaceutically acceptable salts thereof and any combinations. In a more typical embodiment, the BER inhibitor can be methoxyamine (MX). In a most typical embodiment, the BER inhibitor can be methoxyamine (MX) and the anticancer agent can be pemetrexed. For example, the pemetrexed can be the disodium salt of pemetrexed. In an exemplary embodiment the pemetrexed can be the disodium salt heptahydrate.

Some embodiments provide a method of treating cancer, comprising providing a first formulation containing an anticancer agent and a second formulation containing a BER inhibitor that can be administered separately or as a combined formulation selecting an subject diagnosed with cancer, wherein said cancer is resistant to treatment with the anticancer agent alone or in combination with other anticancer agents;

administering said first formulation and said second formulation;

wherein the amount of said first formulation and the amount of said second formulation can be in a amount that when administered to said subject the anticancer effect can be greater than the anticancer effect of the first formulation alone.

In some embodiments, the first formulation can comprise an anticancer agent selected from the group consisting of pemetrexed, capecitabine, edatrexate, methotrexate, lometrexol, nolatrexed, ralitrexed, PT523, trimetrexate, aminopterin, pharmaceuticals salts thereof and any combinations. In a typical embodiment, the anticancer agent can be pemetrexed. In some embodiments, the second formulation can comprise a BER inhibitor selected from the group consisting of methoxyamine (MX), N-ethylmaleimide, $O^6$-benzylguanine, pharmaceutically acceptable salts thereof and any combinations. In a typical embodiment the BER inhibitor can be methoxyamine.

In some embodiments, the anticancer agent can be administered in a dose of from about 25 mg/m² to about 5,000 mg/m² body surface area. For example, the dose can be from about 25 mg/m² to about 200 mg/m² body surface area; the dose can be from about 150 mg/m² to about 500 mg/m² body surface area; the dose can be from about 400 mg/m² to about 1000 mg/m² body surface area; the dose can be from about 900 mg/m² to about 5,000 mg/m² body surface area; the dose can be from about 200 mg/m² to about 1,000 mg/m² body surface area; or the dose can be from about 500 mg/m² to about 600 mg/m² body surface area. In some embodiments, the anticancer agent can be selected from the group consisting of pemetrexed, capecitabine, edatrexate, methotrexate, lometrexol, nolatrexed, ralitrexed, PT523, and trimetrexate. In a more typical embodiment, the anticancer agent can be pemetrexed and pharmaceutically acceptable salts thereof. For example, the pemetrexed can be the disodium salt. In an exemplary embodiment the pemetrexed can be the disodium salt heptahydrate.

In some embodiments, the ratio of BER inhibitor to anticancer agent can be from about 1:2 to about 1:10000. For example, ratio of BER inhibitor to anticancer agent can be from about 1:2 to about 1:1100; ratio of BER inhibitor to anticancer agent can be from about 1:50 to about 1:500; ratio of BER inhibitor to anticancer agent can be from about 1:450 to about 1:10000; ratio of BER inhibitor to anticancer agent can be from about 1:5 to about 1500; ratio of BER inhibitor to anticancer agent can be from about 1:10 to about 1:50; the ratio of BER inhibitor to anticancer agent can be from about 1:15 to about 1:40; or the ratio of BER inhibitor to anticancer agent can be from about 1:20 to about 1:30. In a typical embodiment the BER inhibitor can be selected form the group consisting of methoxyamine (MX), N-ethylmaleimide, $O^6$-benzylguanine, pharmaceutically acceptable salts thereof and any combinations. In a more typical embodiment, the BER inhibitor can be methoxyamine (MX).

Some embodiments provide a method of treating cancer, comprising providing a first formulation containing an anticancer agent and a second formulation containing a BER inhibitor that can be administered separately or as a combined formulation;

selecting a subject diagnosed with cancer;

administering said first formulation and said second formulation;

wherein the amount of said first formulation and the amount of said second formulation can be in a amount that when administered to said subject the anticancer effect can be greater than the added anticancer effect of the first formulation containing an anticancer agent and the second formulation containing a BER inhibitor.

In some embodiments, the first formulation can comprise an anticancer agent selected from the group consisting of pemetrexed, capecitabine, edatrexate, methotrexate, lometrexol, nolatrexed, ralitrexed, PT523, trimetrexate, aminopterin, pharmaceuticals salts thereof and any combinations. In a typical embodiment, the anticancer agent can be pemetrexed. In some embodiments, the second formulation can comprise a BER inhibitor selected from the group consisting of methoxyamine (MX), N-ethylmaleimide, $O^6$-benzylguanine, pharmaceutically acceptable salts thereof and any combinations. In a typical embodiment the BER inhibitor can be methoxyamine.

In some embodiments, the anticancer agent can be administered in a dose of from about 25 mg/m² to about 5,000 mg/m² body surface area. For example, the dose can be from about 25 mg/m² to about 200 mg/m² body surface area; the dose can be from about 150 mg/m² to about 500 mg/m² body surface area; the dose can be from about 400 mg/m² to about 1000 mg/m² body surface area; the dose can be from about 900 mg/m² to about 5,000 mg/m² body surface area; the dose can be from about 200 mg/m² to about 1,000 mg/m² body surface area; or the dose can be from about 500 mg/m² to about 600 mg/m² body surface area. In some embodiments, the anticancer agent can be selected from the group consisting of pemetrexed, capecitabine, edatrexate, methotrexate, lometrexol, nolatrexed, ralitrexed, PT523, and trimetrexate. In a more typical embodiment, the anticancer agent can be pemetrexed and pharmaceutically acceptable salts thereof. For example, the pemetrexed can be the disodium salt. In an exemplary embodiment the pemetrexed can be the disodium salt heptahydrate.

In some embodiments, the ratio of BER inhibitor to anticancer agent can be from about 1:2 to about 1:10000. For example, ratio of BER inhibitor to anticancer agent can be from about 1:2 to about 1:100; ratio of BER inhibitor to anticancer agent can be from about 1:50 to about 1:500; ratio of BER inhibitor to anticancer agent can be from about 1:450 to about 1:10000; ratio of BER inhibitor to anticancer agent can be from about 1:5 to about 1:500; the ratio of BER inhibitor to anticancer agent can be from about 1:10 to about 1:50; the ratio of BER inhibitor to anticancer agent can be from about 1:15 to about 1:40; or the ratio of BER inhibitor to anticancer agent can be from about 1:20 to about 1:30. In a typical embodiment the BER inhibitor can be selected form the group consisting of methoxyamine (MX), N-ethylmaleimide, $O^6$-benzylguanine, pharmaceutically acceptable salts thereof and any combinations. In a more typical embodiment, the BER inhibitor can be methoxyamine (MX).

Another aspect of the current embodiment is the unexpected showing that certain BER inhibitors act synergistically in combination with certain antifolates to unexpectedly reverse resistance to certain antifolates. Thus, in non-limiting preferred embodiments, the antimetabolite anticancer agent is an antifolate anticancer agent. These antifolates disrupt folate-dependent metabolic processes essential to cell replication. Antifolates are distinct from other chemotherapeutics in that they act to disrupt cellular processes involved in folate metabolism. These include the inhibition of folate dependent enzymes, including, but not limited to thymidylate synthase (TS). Interruption of folate-dependent processes leads to improper DNA replication and apoptosis of rapidly dividing cells, including cancer cells. In one embodiment, the ratio of MX to antimetabolite anticancer agent is between about 1:5 and 1:500. In certain embodiments the ratio of MX to antimetabolite anticancer agent is between about 1:10 and about 1:100, between about 1:25 and about 1:75, between about 1:15 and about 1:40, or between about 1:20 and about 1:30. In addition, a second anticancer agent may be administered prior to or after the combination of MX and antimetabolite anticancer agent.

Pharmaceutical Compositions

It will be appreciated that compositions provided herein may be in any form which allows for the composition to be administered to a patient. For example, the composition may be in the form of a solid, liquid or gas (e.g., aerosol). Other suitable routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrathecal, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Opthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1): 101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg/m$^2$ and 2000 mg/m$^2$ body surface area per day of each active ingredient, typically between 1 mg/m$^2$ and 500 mg/m$^2$ body surface area per day, for example 5 mg/m$^2$ to 200 mg/m$^2$ body surface area per day. In other embodiments, an intravenous, subcutaneous, or intramuscular dose of each active ingredient of between 0.01 mg/m$^2$ and 100 mg/m$^2$ body surface area per day, typically between 0.1 μm$^2$ mg and 60 mg/m$^2$ body surface area per day, for example, 1 mg/m$^2$ to 40 mg/m$^2$ body surface area per day can be used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg/m$^2$ body surface area per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, typically between 30-90% and most typically between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the L compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

Throughout the specification, any recitation of a particular compound should be understood to encompass that compound and any (other) pharmaceutically acceptable salts thereof.

In the first step of BER, a series of glycosylases recognize abnormal bases such as N$^3$ mA and N$^7$ mG (O'Connor et al. "Isolation and structure of a cDNA expressing a mammalian 3-methyladenine-DNA glycosylase" *EMBO J.* 9:3337-3342, 1990; Samson et al. "Cloning and characterization of a 3-methyladenine DNA glycosylase cDNA from human cells whose gene maps to chromosome 16" *Proc. Natl. Acad. Sci. USA* 88:9127-9131, 1991), the T:G mismatch (Neddermann et al. "Functional expression of soluble human interleukin-11 (IL-11) receptor alpha and stoichiometry of in vitro IL-11 receptor complexes with gp130" *J. Biol. Chem.* 271:12767-

12774, 1996), and deaminated bases such as hypoxanthine/ oxidized 8-oxo-7,8-dihydroguanine or uracil:A (Vollberg et al. "Isolation and characterization of the human uracil DNA glycosylase gene" *Proc. Natl. Acad. Sci. USA* 86: 8693-8697, 1989; Olsen et al. "Molecular cloning of human uracil-DNA glycosylase, a highly conserved DNA repair enzyme" *EMBO J.* 8:3121-3125, 1989; Radicella et al. "Cloning and characterization of hOGG1, a human homolog of the OGG1 gene of *Saccharomyces cerevisiae*" *Proc. Natl. Acad. Sci. USA* 94.8010-8015, 1997; Rosenquist et al. "Cloning and characterization of a mammalian 8-oxoguanine DNA glycosylase" *Proc. Natl. Acad. Sci. USA* 94:7429-7434, 1997). Following enzymatic or spontaneous hydrolysis of the N-glycosidic bond and release of the abnormal base, AP (apurinic/apyrimidinic) endonuclease hydrolyzes the phosphodiester backbone 5' to the lesion and dRpase (a DNA deoxyribophosphodiesterase and its activity is associated with polymerase β) excises the residual dRp, generating a gap of one nucleotide. DNA polymerase β fills the gap and DNA ligase seals the nick. This pathway is called short-patch BER. An alternative pathway for BER involves DNA synthesis to fill a gap of 2 to 13 nucleotides. This long patch repair requires proliferating cell nuclear antigen (PCNA) and PCNA-dependent DNA polymerase (Wilson "Mammalian base excision repair and DNA polymerase beta" *Mutation Res.* 407:203-215, 1998).

Figure 6:
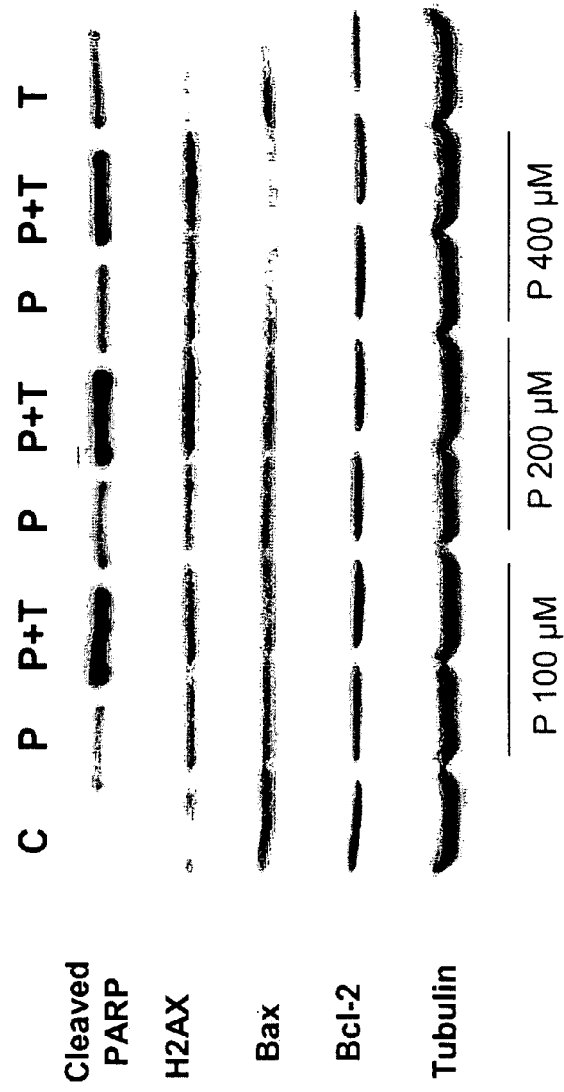
FIG. 6 shows the effect of Pemetrexed and MX in combination on DNA double strand breaks and apoptosis.

Poly-(ADP-ribose)-polymerise (PARP) acts as a nick sensor of DNA strand breaks by itself or interaction with XRCC1 and involves in BER. PARP binds damaged DNA, resulting in autoribosylation. The modified protein then releases and allows other proteins to access and repair DNA strand breaks (Wilson "Mammalian base excision repair and DNA polymerase beta" *Mutation Res.* 407:203-215, 1998; Molinete et al. "Over production of the poly (ADP-ribose) polymerase DNA-binding domain blocks alkylation-induced DNA repair synthesis in mammalian cells" *EMBO J.* 12:2109-2117, 1993; Caldecott et al. "XRCCI polypeptide interacts with DNA polymerase β and possibly poly (ADP-ribose) polymerase, and DNA ligase III is a novel molecular 'nick-sensor' in vitro" *Nucleic Acids Res.* 24:4387-4394, 1996). Therefore, PARP participates in BER after nick formation in both short patch and long patch repair. It appears most active in the alternative (long patch repair) pathway for BER. FIG. 6 shows the combination of Pemetrexed and MX enhances the formation of cleaved PARP. The enhancement of DNA double strand breaks and apoptosis is independent of the Bcl-2 pathway.

Generally, the nomenclature used hereafter and the laboratory procedures in cell culture, tissue culture, tumor biology, and molecular genetics described below are those well known and commonly employed in the art. Standard techniques are used for cell culture methods, experimental design and compound formulation and nomenclature. Generally chemical reactions and purification steps are performed according to the manufacturer's specifications. The techniques and procedures are generally performed according to conventional methods in the art and various general references (see, generally, Sambrook et al. *Molecular Cloning. A Laboratory Manual,* 2d ed. (1989) Cold Spring Harbor Laboratory Press, Cold Spring Harbor, N.Y., and *Current Protocols in Molecular Biology* (1996) John Wiley and Sons, Inc., N.Y., which are incorporated herein by reference) which are provided throughout this document. All the information contained therein is incorporated herein by reference.

Pemetrexed (2-[4-[2-(4-amino-2-oxo-3,5,7-triazabicyclo [4.3.0]nona-3,8,10-trien-9-yl)ethyl]benzoyl]aminopentanedioic acid) (ALIMTA™; Eli Lilly & Co.) is an antimetabolite chemotherapeutic agent that has the following structure:

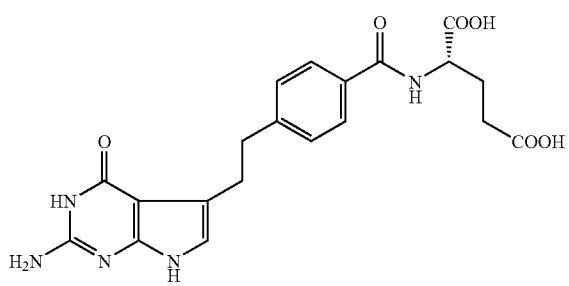

Pemetrexed is an antifolate antineoplastic agent that exerts its action by disrupting folate-dependent mechanisms necessary for cell replication. Pemetrexed inhibits thymidylate synthase (TS), dihydrofolate reductase (DHFR) and glycinamide ribonucleotide formyltransferase (GARFT), enzymes involved in the de novo biosynthesis of thymidine and purine nucleotides. Pemetrexed is approved by the FDA for the treatment of non-small cell lung cancer and approved in combination with cisplatin (a platinum-based chemotherapy drug) for treatment of malignant pleural mesothelioma. The recommended dose for treatment of mesothelioma (in combination with cisplatin) or non-small cell lung cancer is about 500 mg/m$^2$ body surface area per day administered as an intravenous infusion over 10 minutes on Day 1 of each 21-day cycle. For use in combination therapy with methoxyamine, typical dosage ranges of pemetrexed are generally between 200 mg/m$^2$ and 1,000 mg/m$^2$ body surface area per day, or between 500 mg/m$^2$ and 600 mg/m$^2$ body surface area per day; and typical dosage ranges of methoxyamine are between 1 and 200 mg/m$^2$ body surface area per day, or 6 to 120 mg/m$^2$ body surface area per day. In one embodiment, pemetrexed is administered in the same manner as described above; however, the intravenous infusion may be performed over 15 min, 20 min, 30 min, 45 min, 60 min or longer, and may be performed on Day 1, plus one or more additional days of a given cycle which may be 1 week, 2 weeks, three weeks, one month or longer.

EXAMPLES

Materials and Methods

Chemicals and Reagents. Methoxyamine (MX) was purchased from Sigma (ST. Louis, Mo.). MX was dissolved in sterilized water (pH 7.0).

Western Blotting for PARP Cleavage Detection. Cell extracts were resolved by SDS-PAGE (12% polyacrylamide) in a Bio-Rad minigel apparatus at 150 V for 1 hr. Proteins were transferred onto PVDV membranes, using a Bio-Rad mini Trans-Blot cell for 1 hr at 100 V. The blotted membranes were blocked with 5% dry milk in 15 TBS buffer and then probed for 2 hr with anti-PARP antibody $C_{2-10}$ (Trevigen, Gaithersburg, Md.). After three 5 min washes with TBS-Tween20 (0.05%), the blots were incubated with secondary antibody, anti-mouse HRP-anti IgG for 1 hr (Amersham Life Science, Arlington Height Ill.). Antibody binding was visualized by ECL according to manufacturer's instructions (Amersham Life Science, Arlington Heights, Ill.).

Tumors in Nude Mice. Tumor cells ($5\times10^6$) were injected into flanks of female athymic HSD nude mice, at 6-8 weeks of age. Animals received five daily intraperitoneal injections of either saline, pemetrexed alone (150 mg/kg), MX alone (4 mg/kg), or a combination of pemetrexed (150 mg/kg) and MX (4 mg/kg) with a pemetrexed to MX ratio of 26.7:1.0. Tumors were measured with calipers using the National Cancer Institute formula: $V=L(mm)\times I^2$ (mm)/2 where L is the largest diameter and I is the smallest diameter of the tumor. When the volume of the nodules had achieved about 100-150 $mm^3$, tumor-bearing mice were assigned randomly for the control or treatment groups (6-9 mice/group).

Example 1

Figure 8:
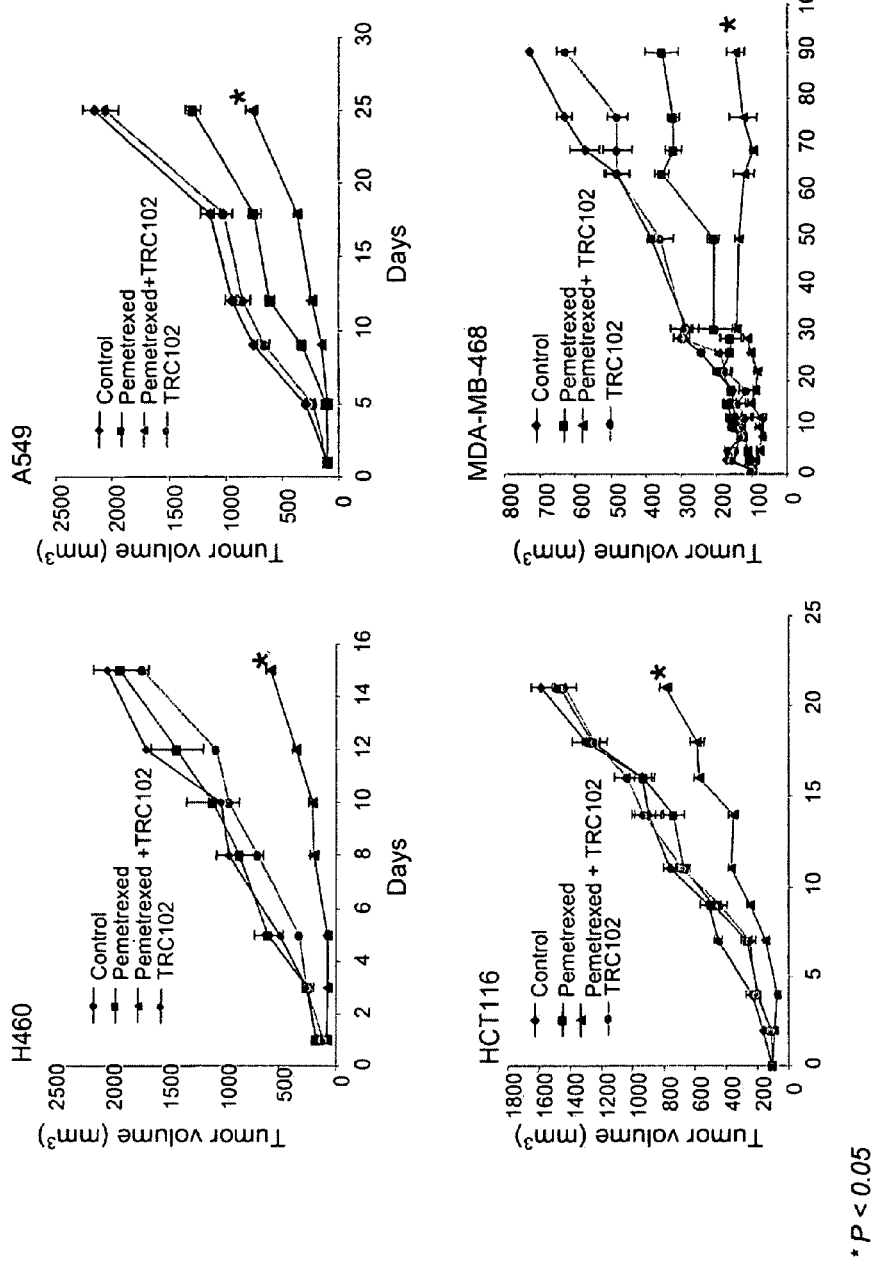
FIG. 8 shows the effect of Pemetrexed and MX on the median volume of NCI-H460 tumors, A549 tumors, HCT116 tumors, and MDA-MB-468 tumors grown in nude mice.

FIG. 8 shows all groups receiving Methoxyamine (MX)+pemetrexed exhibited greater tumor growth delay compared to groups receiving only pemetrexed in the human NCI-H460 NSCLC cell line model, A549 NSCLC cell line model, HCT116 colon cancer cell line model and MDA-MB-468 breast cancer cell line model. MX reversed resistance of the NCI-H460 NSCLC cell line and HCT116 colon cancer cell line to the effects of pemetrexed chemotherapy.

Example 2

Figure 4B:
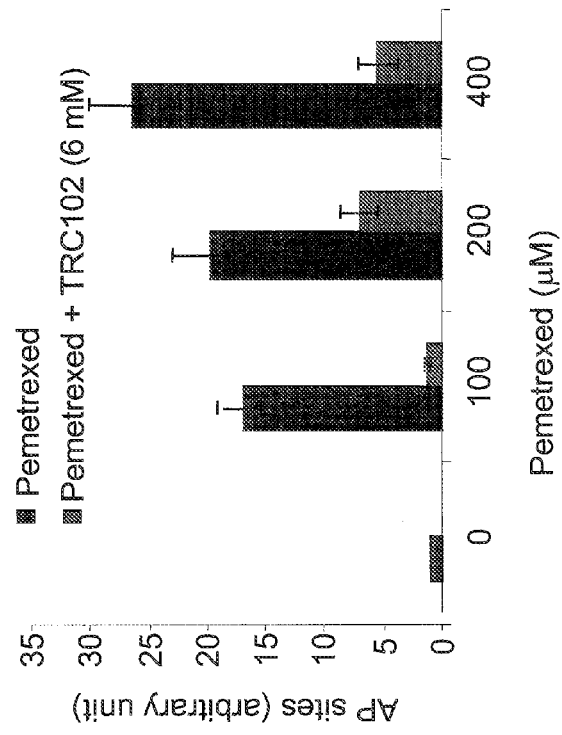
FIG. 4B is a graph showing the relative amount of AP sites detected in H460 cells at 24 hrs, 48 hrs and 72 hrs.

To determine the effect of pemetrexed+methoxyamine (MX) compared to pemetrexed alone on the number of AP sites generated, an aldehyde reactive probe (ARP) reagent was used to measure AP sites formed by pemetrexed and blocked by MX. ARP and MX have a similar reactivity with AP sites, and react specifically with an aldehyde group, an open-ring form of the AP sites. The assay is described in Liu et al. (*Molecular Cancer Therapeutics* 2:1061-1066, 2003), and was performed essentially as described by Nakamura et al. (*Cancer Res.* 58:222-225, 1998). H460 cells were treated with pemetrexed (0, 100, 200 or 400 µm) for 24 hours. DNA (15 µg) was then extracted from cells and incubated with 1 mM ARP at 37° C. for 10 min. DNA was precipitated and washed with ethanol, then resuspended in TE buffer (10 mM Tris-HCl, pH 7.2, 1 mM EDTA) and denatured at 100° C. for 5 min. The DNA was then quickly chilled on ice and mixed with an equal amount of ammonium acetate (2 M). Single-stranded DNA was then immobilized on a nitrocellulose membrane using a vacuum filter device. The membrane was incubated with streptavidin-conjugated horseradish peroxidase at room temperature for 30 min and rinsed with washing buffer (20 mM Tris-HCl, 1 mM EDTA, 0.26 M NaCl, 1% Tween-20). ARP-AP sites were visualized with ECL reagents (Amersham, Piscataway, N.J.). The results are shown in 4A. Pemetrexed at doses of 100, 200 and 400 µM induced the formation of AP sites, with the degree of AP site induction proportional to pemetrexed dose (FIG. 4A). The addition of MX to pemetrexed significantly reduced the number of detectable AP sites compared to pemetrexed alone. The effect of the combination of 200 µM pemetrexed and 6 mM MX was viewed at 24 hrs, 48 hrs and 72 hrs. The results are shown in FIG. 4B. Over time the number of detectable AP sites were reduced with both pemetrexed alone and pemetrexed in combination with MX.

In summary, pemetrexed induces the formation of AP sites, while the combination of pemetrexed and 100 µM MX reduced detectable AP sites to control levels which is due, not to the absence of AP sites, but to the occupancy of AP sites by MX, making them unavailable for ARP. Occupancy of AP sites is time dependent, indicating the sustained levels of MX are needed for maximal effect.

Example 3

A DNA strand break assay was performed to determine the ability of pemetrexed and methoxyamine (MX) to increase tumor cell death mediated by apoptosis and DNA strand break. The Comet assay is described in Liu et al. (supra.), and is based on the ability of denatured, cleaved DNA fragments to migrate out of the cell under influence of an electric field. Undamaged DNA migrates slower and remains within the confines of the nuclei when a current is applied. DNA damage was assessed in a cell based on evaluation of the DNA "comet" tail shape and migration distance (Helma et al., *Mutat. Res.* 466:9-15, 2000). Cells were harvested and washed with PBS after exposure to 200 µM pemetrexed, 6 mM MX, or 200 µM pemetrexed+6 mM MX, each for 4 hours. A suspension of H460 cells ($1\times10^5$/ml cold PBS) was mixed with 1% low gelling temperature agarose at 42° C. at a ratio of 1:10 (v/v) and 75 µl was immediately pipetted onto CometSlide (Trevigen, Inc., Gaithersburg, Md.). When the low gelling temperature agarose had set, the slides were submerged in prechilled lysis buffer (10 mM Tris-HCl, pH 10.5-11.5, 2.5 M NaCl, 100 mM EDTA, containing 1% Triton X-100, added just before use) at 4° C. for 1 h. After lysis, the slides were washed with distilled water, arranged lengthwise in an electrophoresis tank and submerged in alkali buffer (50 mM NaOH, pH 12-12.5, 1 mM EDTA) for 30 min. Slides were then electrophoresed in both alkali (pH>13, 300 mM NaOH, 1 mM EDTA) and neutral solution (1×TBE) for 25 min at 18 V (0.6 V/cm), 250 mA. Alkaline electrophoresis detects both single-and double-stranded DNA breaks, resulting from AP sites as well as other alkali labile DNA adducts, whereas neutral electrophoresis detects predominantly double-stranded DNA breaks. The slides were removed and washed with neutralization buffer (0.5 M Tris-HCl, pH 7.5) for 10 min, then with PBS, then left to air dry overnight at room temperature. The DNA was stained using silver Staining Kit (Trevigen), following the manufacturer's instructions. Comets were visualized using an Olympus microscope. Images were captured using a digital camera and analyzed using NIH image software.

Comet images are shown in FIGS. 1A (alkaline assay) and 1B (neutral assay). After treatment with pemetrexed and MX, distinct comets were observed, and the tail length was about 4 times greater than with MX alone, and about two times greater than with pemetrexed alone (FIGS. 1C-D).

The results from the xenograft efficacy study, AP site assay and Comet assay show that MX acts as a structural modulator of AP sites, enhancing the therapeutic effect of the antimetabolite agent pemetrexed by reversing resistance to the chemotherapy, thereby producing a synergistic effect.

Example 4

Figure 5:
FIG. 5A shows a schematic diagram of the preparation of DNA substrates with regular AP sites or MX-AP sites.
FIG. 5B shows that MX-bound AP sites are resistant to cleavage by AP-endonuclease (APE).

Analysis of the effect of AP site or MX-AP site on topoisomerase II-mediated DNA cleavage. A position-specific apurinic site was incorporated by replacing a single nucleoside with deoxyuridine at a topoisomerase II cleavage site and then removing the uracil base with uracil-DNA glycosylase, generating AP sites that further are incubated with MX to produce MX-AP sites (FIG. 5A).

First, it was determined whether APE has a differential effect between regular AP sites and MX-AP sites located in a position specific site for topo II cleavage. Results show that APE is able to cleave regular AP sites rather than MX-bound AP sites (FIG. 5B), however, both AP and MX-AP sites are cleaved by topoisomerase II, indicating MX-AP sites are able to stimulate topoisomerase II-mediated DNA cleavage.

Example 5

Oral and Intravenous Bioavailability Study of MX Via a Single Bolus Administration to Sprague Dawley Rats (Non-GLP). The studies described below were performed to evaluate the bioavailability of methoxyamine (MX) at the safe dose level by comparison of the pharmacokinetic parameters after single bolus oral and intravenous administrations of MX Test Animals. Thirty male and thirty female Sprague Dawley rats, 250-350 g, 7-10 weeks of age, were used during the study.

Dose Preparation and Concentration. One dose solution was prepared on the same day of dose administration, adjusted for the 98% purity of the test article, to achieve a concentration of 4.00 mg/mL "active" MX, 816.77 mg of MX was dissolved into 5% dextrose in a 200-mL volumetric flask. The prepared solution was equally divided into two amber bottles designated for either oral or IV administration. Aliquots were taken for analysis at preparation and after dosing, transported on dry ice and stored at <−70° C.

Dose Administration. All animals were weighed on the day of dose administration. Individual animal doses were based on this body weight. A constant dose volume of 5 mL/kg was used. IV doses were administered through a single bolus injection into the tail vein using a 3-mL syringe attached to a 26G×1" needle. The IV dose was administered at a rate of approximately 2 mL/min. Oral doses were administered as a single bolus with an 18G×2" feeding needle attached to a 3-mL syringe.

Blood Sample Collection. Blood samples were collected at 5, 15, 30 mins, and 1, 2, 4, 6, 8, 12 and 24 hrs post-dose, with collection at two time points for each animal. Blood samples were collected through the jugular vein for the earlier time point and through the abdominal vein at sacrifice for the later time point. The blood was transferred from the drawing syringe into a 2 mL blood collection tube containing $K_3$-EDTA as the anticoagulant and inverted to mix. Abdominal vein blood collection was performed immediately following $CO_2$ euthanasia.

Plasma Sample Preparation and Storage Conditions. The blood tube was placed on wet ice before centrifugation for plasma preparation. Whole blood samples were centrifuged at 3,000 rpm at 4° C., for 10 min. Plasma was pipetted into tubes and placed on dry ice initially and later stored at <−70° C.

Mass spectrometry (MS). Mass spectrometric detection was performed by electrospray ionization with positive turbo spray, according to the specifications listed below.

MS Instrument: Applied Biosystems 3000
HPLC Instrument: Agilent 1100 Series Binary Pump
Autosampler: LEAP Technologies CTC-PAL

| Electrospray Ionization (ESI) Conditions: | |
|---|---|
| Temperature: | 500° C. |
| Nebulizer Gas: | Nitrogen |
| CAD Gas: | Nitrogen |
| DP: | 40 |
| Curtain Gas (CUR): | 10 |
| Collision Gas: | 6 |
| Ion Spray Voltage (IS): | 5000 |

-continued

| | |
|---|---|
| Exit Potential (EP): | 10 |
| NEB: | 12 |
| Monitor: | |
| Analyte: | 207.0/149.3 and 207.0/178.4 amu |
| IS (Acenocoumerol): | 354.2/296.0 and 354.2/163.1 amu |

HPLC Conditions (on Agilent 1100):
Mobile phase A: 0.1% Formic Acid in Water
Mobile phase B: 0.1% Formic Acid in Acetonitrile
Column: Thermo Aquasil C18, 50×3 mm
Guard Column: Thermo Aquasil C18, 10×4 mm
Flow Rate: 1.0 mL/min
Injection Volume: 50 μL
Gradient:

| Time (min) | % B |
|---|---|
| 0.0 | 0% |
| 2.0 | 10% |
| 2.2 | 90% |
| 4.5 | 90% |
| 4.6 | 0% |
| 5.6 | 0% |

Plasma Sample for LC-MS/MS Analysis. Individual plasma samples were thawed at ambient temperature and 250 μL was aliquoted for analysis if a dilution was not needed. Samples taken at 5 min to 1 hr from IV dosed animals or 15 min to 8 hr from orally dosed animals required 5-to 40-fold dilution to fall in the linear range of the method (1 to 1,000 ng/mL). For the samples requiring dilution, an appropriate volume was taken and mixed with blank rat plasma containing the same anticoagulant to make a total volume of 250 μL. The quantitation results were corrected with the dilution factor. Plasma was prepared for LC-MS/MS analysis as follows:

Plasma aliquots were vortexed for 30 seconds, and centrifuged at 14,000 rpm for 10 min to precipitate the interfering particles.

A 100 μL aliquot was taken from the supernatant and placed into a 1.5 mL microcentrifuge tube.

To the 100 μL plasma aliquot, 310 μL of $H_2O$: formic acid (2:1), 30 μL of acenocoumerol (IS) in $H_2O$ (10 μg/mL) and 100 μL of diethylaminobenzaldehyde in 2:1$H_2O$: formic acid solution (10 mg/mL) were added and mixed well.

The mixture was then incubated in a water bath at 80° C. for 2 hrs. After incubation, the supernatant was transferred into a HPLC vial for LC-MS/MS quantitation.

Methoxyamine (MX) Pharmacokinetics and Bioavailability Analysis. Pharmacokinetics Analysis. Methoxyamine (MX) pharmacokinetic (PK) profiles and oral bioavailability was determined in male and female Sprague Dawley rats after a single bolus dosing of MX via intravenous and oral administration at 20 mg/kg body weight. Thirty rats (15 male and 15 female) of each dosing route were used in the pharmacokinetic analysis. Plasma samples, for MX pharmacokinetic characterization purposes, were obtained at the nominal sampling times of predose, 5, 15, 30 mins and 1, 2, 4, 6, 8, 12 and 24 hrs after the dose administration. To maintain normal health conditions, each rat had a maximum of two blood draws at the predetermined time point to generate plasma. The representative MX concentration was obtained by averaging the values from the three rats for each time point within the same sex and dosing route. For the mean dose amount, mean actual sampling times were obtained correspondingly from the three rats for each nominal time point within the same sex and dosing route. The mean plasma MX concentration, mean dose amount, and mean actual sampling time were used for pharmacokinetic analysis for each dosing route.

Mean plasma MX concentration vs. mean sample time curves were constructed for each sex and dosing route using Microsoft Excel 2000-SR1™ (FIGS. 2-3). Plasma MX concentrations reported as below quantifiable limits (BQL) or non-detectable, if any, were considered as 0.00 ng/mL for pharmacokinetic modeling purposes.

Pharmacokinetic parameter analysis was performed using noncompartmental modeling via WinNonlin 5.1 (Pharsight Corporation, Mountain View, Calif.). Pharmacokinetic parameters included maximal plasma concentration ($C_{max}$), time of maximal plasma concentration ($T_{max}$), elimination half-life ($t_{1/2}$), area under the plasma concentration vs. time curve from time zero to the last measurable plasma concentration ($AUC_{last}$) and area under the plasma concentration vs. time curve from time zero extrapolated to infinity ($AUC_{0-\infty}$). For comparison, the $AUC_{0-\infty}$ was normalized to a nominal total MX dose amount of 5 mg ($AUC_{0-\infty 5}$). Pharmacokinetic parameters were abbreviated as previously stated.

Bioavailability Analysis. Absolute oral bioavailability was determined by the oral to IV methoxyamine (MX) $AUC_{0-\infty}$ ratios (normalized to the total dose amount of 5 mg of MX) with Microsoft Excel 2000-SR1™ using the following equation (MX=TRC102):

$$\text{Absolute Oral TRC102 Bioavailability}(\%) = \frac{(\text{IV Dose}) * (\text{Oral } AUC_{0-\infty})}{(\text{Oral Dose}) * (\text{IV } AUC_{0-\infty})} \times 100$$

The actual dose levels of MX were 20.1 mg/kg, 20.1 mg/kg for male and female rats in IV dosing group, and 19.9 mg/kg, 20.0 mg/kg for male and female rats in oral dosing groups, respectively.

Pharmacokinetics and Bioavailability. Methoxyamine (MX) pharmacokinetic parameters for male and female Sprague Dawley rats, after a single bolus dosing of MX via intravenous and oral administration at 20 mg/kg body weight, are outlined in Table 1.

TABLE 1

MX Pharmacokinetic Parameters in Plasma from Male and Female Sprague Dawley Rats After a Single Bolus Dosing of MX via Intravenous and Oral Administration at 20 mg/kg Body Weight

|  | Male | | Female | |
| --- | --- | --- | --- | --- |
|  | IV | Oral | IV | Oral |
| Mean Total Dose Amount of MX (mg) | 5.63 | 5.56 | 4.73 | 4.61 |
| $C_{max}$ (ng/mL) | 15510 | 2205 | 10965 | 2959 |
| $T_{max}$ (hr) | 0.08 | 1.0 | 0.08 | 0.50 |
| $t_{1/2}$ (hr) | 5.2 | 4.2 | 4.6 | 5.7 |
| $AUC_{last}$ (ng/mL*hr) | 12518 | 13596 | 12971 | 11643 |
| $AUC_{0-\infty}$ (ng/mL*hr) | 12706 | 13811 | 13142 | 12029 |
| $AUC_{0-\infty}5$ (ng/mL*hr)[a] | 11284 | 12420 | 13892 | 13047 |
| Bioavailability (%) |  | 110 |  | 94 |
| F |  | 1.1 |  | 0.94 |

[a]$AUC_{0-\infty}5$ (ng/mL*hr) is obtained by normalizing the $AUC_{0-\infty}$ (ng/mL*hr) to a total dose amount of 5 mg MX.

For male rats, there were quantifiable MX concentrations in plasma throughout the entire 24-hr sampling period, for both the intravenous and oral administrations. Visual inspection of the male intravenous mean plasma MX concentration versus mean time curve suggests a rapid distribution phase which was complete at approximately 2 hrs postdose. The intravenous route $C_{max}$ was 15,510 ng/mL and occurred immediately upon completion of the bolus administration. Systemic MX exposure, as indicated by $AUC_{last}$ and $AUC_{0-\infty}$, was 12,518 ng/mL*hr and 12,706 ng/mL*hr respectively. The intravenous $AUC_{0-\infty}$ adjusted to the total nominal dose amount of 5 mg ($AUC_{0-\infty}$) was 11,284 ng/mL*hr.

For the male rats in oral dosing route, MX absorption was rapid with a $T_{max}$ of 1.0 hr. The $C_{max}$ of 2,205 ng/mL was considerably less than that of the intravenous dosing route. Systemic MX exposure, as indicated by oral $AUC_{last}$ and $AUC_{0-\infty}$, was 13,596 ng/mL*hr and 13,811 ng/mL*hr respectively. The oral $AUC_{0-\infty}$ adjusted to the nominal total dose amount of 5 mg ($AUC_{0-\infty 5}$) was 12,420 ng/mL*hr. Elimination half-lives were short and similar between the two dosing routes (IV: 5.2 hr, Oral: 4.2 hr). The calculated absolute bioavailability through oral administration in male Sprague Dawley rats was 110 percent.

For female rats, there were quantifiable MX plasma concentrations, throughout the entire 24-hr sampling period, for both the intravenous and oral dosing routes. Visual inspection of the female intravenous mean plasma MX concentration versus mean time curve suggests a rapid distribution phase which appears, like the male rats, complete at approximately 2 hrs postdose. The intravenous route $C_{max}$ was 10,965 ng/mL and occurred immediately upon completion of the bolus administration. Systemic MX exposure, as indicated by $AUC_{last}$ and $AUC_{0-\infty}$, was 12,971 ng/mL*hr and 13,142 ng/mL*hr, respectively. The intravenous $AUC_{0-\infty}$ adjusted to the nominal total dose amount of 5 mg ($AUC_{0-\infty 5}$) was 13,892 ng/mL*hr.

For the female rats in oral dosing route, MX absorption was rapid with a $T_{max}$ of 0.5 hr. The $C_{max}$ of 2959 ng/mL was considerably less than the intravenous route, yet similar to that of the male rats in oral dosing route. Systemic MX exposure, as indicated by oral $AUC_{last}$ and $AUC_{0-\infty}$, was 11,643 ng/mL*hr and 12,029 ng/mL*hr respectively. The oral $AUC_{0-\infty}$ adjusted to the nominal total dose amount of 5 mg ($AUC_{0-\infty 5}$) was 13,647 ng/mL*hr. Elimination half-lives were rapid, similar between the two dosing routes (IV: 4.6 hr, Oral: 5.7 hr), and comparable to those of the male rats. The calculated absolute bioavailability in female Sprague Dawley rats was 94 percent.

Rats dosed with 20 mg/kg body weight (BW) given both intravenously or orally showed no clinical signs of toxicity.

In both male and female Sprague Dawley rats, MX administered at 20 mg/kg BW via a single bolus oral administration is rapidly ($T_{max}$ 0.5-1.0 hr) and completely absorbed with a systemic absolute bioavailability of approximately 100 percent. Although the oral MX $C_{max}$ is significantly less than the IV $C_{max}$, systemic MX exposure, as indicated by $AUC_{last}$ and $AUC_{0-\infty}$, appears to be similar between the two dosing routes. Furthermore, serum levels exceeded the target $C_{max}$ associated with activity in mouse models of human cancer (50 ng/mL) following oral dosing at time points that would permit the use of a single or twice daily oral dosing schedule.

These data are significant in that they indicate that methoxyamine is completely orally bioavailable and has a half life of 4-6 hours that permits the attainment of minimally effective concentrations with single or twice daily dosing. Both of these findings are unexpected. The majority of anticancer agents are not orally bioavailable in sufficient quantities to permit oral dosing. It should be noted that attempts to administer other particular anticancer drugs orally have resulted in a much lower bioavailability than achieved herein. See for example bleomycin, carboplatin, cisplatin, oxaliplatin, paclitaxel, raltitrexed (an antifolate), topotecan, vinblastine, vincristine, vinorelbine all of which have less than 50% bioavailability (Chu E and DeVita V T. Physicians' Cancer Chemotherapy Drug manual 2002. Boston: Jones and Bartlett Publishers, 2002) Second, the half-life demonstrated is longer than expected for a small molecule with molecular mass <100 daltons that readily reacts with aldehydes that may be present in the plasma, and the longer than expected plasma half-life permits sustained drug levels (above the minimal effective concentration) with a single or twice daily oral dosing schedule. The complete bioavailablility and 4 to 6 hour half life, can allow for oral dosing using a single or twice daily dosing schedule that can be convenient to cancer patients.

From the foregoing, it will be obvious to those skilled in the art that various modifications in the above-described methods, and compositions can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore intended to be embraced therein.

Thus, it will be understood that there is no intent in the use of such terms and expressions to exclude any equivalent of the features shown and described or portions thereof, but it is recognized that various modifications are possible within the scope of the invention as claimed. It will also be understood that each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety.

What is claimed is:
1. A method comprising:
providing a subject diagnosed with a cancer selected from non-small cell lung cancer, colorectal cancer, and breast cancer, i) a first formulation comprising pemetrexed and ii) a second formulation comprising methoxyamine;
administering said first formulation to said subject; and
administering said second formulation to said subject wherein the ratio of methoxyamine to pemetrexed is between 1:15 and 1:40.
2. The method of claim 1, wherein said methoxyamine and pemetrexed are administered as a formulation.
3. The method of claim 1, wherein said methoxyamine and pemetrexed are administered sequentially in either order.
4. The method of claim 1, wherein said methoxyamine is administered orally and pemetrexed is administered orally or intravenously.
5. The method of claim 1, wherein the ratio of said methoxyamine to pemetrexed is sufficient to sensitize the cancer cells to pemetrexed.
6. The method of claim 1, wherein said methoxyamine and pemetrexed are administered to achieve a synergistic effect.
7. The method of claim 1, wherein pemetrexed is administered orally or intravenously and methoxyamine is administered orally once or twice daily wherein the ratio of methoxyamine to pemetrexed is sufficient to potentiate the activity of pemetrexed.
8. The method of claim 1, wherein said subject is selected as having a cancer selected from non-small cell lung cancer, colorectal cancer, and breast cancer that is at least partially resistant to treatment with pemetrexed alone, and wherein the ratio of methoxyamine to pemetrexed is effective to potentiate the activity of pemetrexed and overcome said resistance.
9. A method comprising:
providing a subject diagnosed with a cancer selected from non-small cell lung cancer, colorectal cancer, and breast cancer, i) a first formulation comprising pemetrexed and ii) a second formulation comprising methoxyamine;
administering said first formulation to said subject; and
administering said second formulation orally to said subject wherein the ratio of methoxyamine to pemetrexed is between 1:15 and 1:40.
10. The method of claim 9, wherein said methoxyamine and pemetrexed are administered as a formulation.
11. The method of claim 9, wherein said methoxyamine and pemetrexed are administered sequentially in either order.
12. The method of claim 9, wherein pemetrexed is administered orally or intravenously.
13. The method of claim 9, wherein the ratio of said methoxyamine to pemetrexed is sufficient to sensitize the cancer cells to pemetrexed.
14. The method of claim 9, wherein said methoxyamine and pemetrexed are administered to achieve a synergistic effect.
15. The method of claim 9, wherein pemetrexed is administered orally or intravenously and methoxyamine is administered orally once or twice daily wherein the ratio of methoxyamine to pemetrexed is sufficient to potentiate the activity of pemetrexed.
16. The method of claim 9, wherein said subject is selected as having a cancer selected from non-small cell lung cancer, colorectal cancer, and breast cancer that is at least partially resistant to treatment with pemetrexed alone, and wherein the ratio of methoxyamine to pemetrexed is effective to potentiate the activity of pemetrexed and overcome said resistance.
17. A method comprising:
providing a subject diagnosed with a cancer selected from non-small cell lung cancer, colorectal cancer, and breast cancer, wherein said cancer is at least partially resistant to treatment by pemetrexed alone, i) a first formulation comprising pemetrexed; and ii) a second formulation comprising methoxyamine;
administering said first formulation to said subject; and
administering said second formulation to said subject wherein the ratio of methoxyamine to pemetrexed is between 1:15 and 1:40.
18. The method of claim 17, wherein said methoxyamine and said pemetrexed are administered as a formulation.
19. The method of claim 17, wherein said methoxyamine and said pemetrexed are administered sequentially in either order.
20. The method of claim 17, wherein said pemetrexed is administered orally or intravenously.
21. The method of claim 17, wherein the ratio of said methoxyamine to pemetrexed is sufficient to sensitize the cancer cells to pemetrexed.
22. The method of claim 17, wherein said methoxyamine and said pemetrexed are administered to achieve a synergistic effect.
23. The method of claim 17, wherein said pemetrexed is administered orally or intravenously and methoxyamine is administered orally once or twice daily wherein the ratio of methoxyamine to pemetrexed is sufficient to potentiate the activity of said pemetrexed.

24. In a method for treating a cancer selected from non-small cell lung cancer, colorectal cancer, and breast cancer in a subject diagnosed with said cancer comprising administering pemetrexed to the subject, the improvement of administering methoxyamine to the subject wherein the ratio of methoxyamine to pemetrexed is between 1:15 and 1:40 is sufficient to potentiate the toxicity of pemetrexed.

25. The improved method of claim 24, wherein said methoxyamine and pemetrexed are administered as a formulation.

26. The improved method of claim 24, wherein said methoxyamine and said pemetrexed are administered sequentially in either order.

27. The improved method of claim 24, wherein said methoxyamine is administered orally and pemetrexed is administered orally or intravenously.

28. The improved method of claim 24, wherein the ratio of said methoxyamine to pemetrexed is sufficient to sensitize the cancer cells to pemetrexed.

29. The improved method of claim 24, wherein said methoxyamine and pemetrexed are administered to achieve a synergistic effect.

30. The improved method of claim 24, wherein pemetrexed is administered orally or intravenously and methoxyamine is administered orally once or twice daily wherein the ratio of methoxyamine to pemetrexed is sufficient to potentiate the activity of pemetrexed.

31. An anticancer formulation comprising, a dosage form comprising pemetrexed and a dosage form comprising methoxyamine wherein the ratio of methoxyamine to pemetrexed is between 1:15 and 1:40.

32. A method comprising:
providing a subject diagnosed with a cancer selected from non-small cell lung cancer, colorectal cancer, and breast cancer, i) a first formulation comprising pemetrexed and ii) a second formulation comprising methoxyamine;
administering said first formulation to said subject; and
administering said second formulation to said subject wherein the ratio of methoxyamine to pemetrexed is between 1:2 and 1:100.

33. A method comprising:
providing a subject diagnosed with a cancer selected from non-small cell lung cancer, colorectal cancer, and breast cancer, i) a first formulation comprising pemetrexed and ii) a second formulation comprising methoxyamine;
administering said first formulation to said subject; and
administering said second formulation orally to said subject wherein the ratio of methoxyamine to pemetrexed is between 1:2 and 1:100.

34. A method comprising:
providing a subject diagnosed with a cancer selected from non-small cell lung cancer, colorectal cancer, and breast cancer, wherein said cancer is at least partially resistant to treatment by pemetrexed alone, i) a first formulation comprising pemetrexed; and ii) a second formulation comprising methoxyamine;
administering said first formulation to said subject; and
administering said second formulation to said subject wherein the ratio of methoxyamine to pemetrexed is between 1:2 and 1:100.

35. In a method for treating a cancer selected from non-small cell lung cancer, colorectal cancer, and breast cancer in a subject diagnosed with said cancer comprising administering pemetrexed to the subject, the improvement of administering methoxyamine to the subject wherein the ratio of methoxyamine to pemetrexed is between 1:2 and 1:100 is sufficient to potentiate the toxicity of pemetrexed.

36. An anticancer formulation comprising, a dosage form comprising pemetrexed and a dosage form comprising methoxyamine wherein the ratio of methoxyamine to pemetrexed is between 1:2 and 1:100.

* * * * *